(12) United States Patent
Tisdell et al.

(10) Patent No.: US 6,413,997 B1
(45) Date of Patent: Jul. 2, 2002

(54) 3-(SUBSTITUTED PHENYL)-5-(SUBSTITUTED HETEROCYCLYL)-1,2,4-TRIAZOLE COMPOUNDS

(75) Inventors: Francis E. Tisdell, Carmel; Peter L. Johnson; James T. Pechacek, both of Indianapolis; Robert G. Suhr, Greenfield; Donald H. DeVries, Fishers; Carl P. Denny, Indianapolis; Mary L. Ash, Zionsville, all of IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/426,930

(22) Filed: Oct. 22, 1999

Related U.S. Application Data

(60) Provisional application No. 60/105,354, filed on Oct. 23, 1998.

(51) Int. Cl.[7] .................... A01N 43/78; C07D 411/04
(52) U.S. Cl. ............. 514/365; 514/369; 514/370; 514/371; 548/182; 548/183; 548/184; 548/185; 548/186; 548/189; 548/190; 548/195; 548/198; 548/200; 548/201; 548/202; 548/266.2
(58) Field of Search ................ 514/365, 369, 514/370, 371; 548/182, 183, 184, 185, 186, 189, 190, 195, 198, 200, 201, 202

(56) References Cited

U.S. PATENT DOCUMENTS

| | | | |
|---|---|---|---|
| 3,963,731 A | 6/1976 | Novello et al. | 260/294.8 F |
| 3,984,558 A | 10/1976 | Baldwin et al. | 424/263 |
| 4,011,218 A | 3/1977 | Baldwin et al. | 260/250 AH |
| 4,018,793 A | 4/1977 | Stoss et al. | 260/330.5 |
| 4,713,383 A | 12/1987 | Francis et al. | 514/267 |
| 5,284,860 A | 2/1994 | Ozaki et al. | 514/340 |
| 5,380,944 A | 1/1995 | Ozaki et al. | 564/81 |
| 5,482,951 A | 1/1996 | Ozaki et al. | |
| 6,015,826 A | 1/2000 | Pechacek et al. | 514/383 |

FOREIGN PATENT DOCUMENTS

| | | |
|---|---|---|
| AU | 646990 | 4/1991 |
| EP | 559363 | 9/1993 |
| EP | 572142 | 12/1993 |
| EP | 648752 | 4/1995 |
| WO | 9842683 | 10/1998 |
| WO | 9847894 | 10/1998 |

OTHER PUBLICATIONS

B.I. Buzykin et al. "An approach to 1–Aryl–1,2,4–riazoles", SYNTHESIS, vol. 1993, pp. 59–61 (1993).

*Primary Examiner*—Patricia L. Morris
(74) *Attorney, Agent, or Firm*—Craig E. Mixan; Donald R. Stuart

(57) ABSTRACT 3-(Substituted phenyl)-5-(substituted heterocyclyl)-1,2,4-triazole compounds are useful as insecticides and acaricides. New synthetic procedures and intermediates for preparing the compounds, pesticide compositions containing the compounds, and methods of controlling insects and mites using the compounds are also provided.

14 Claims, No Drawings

3-(SUBSTITUTED PHENYL)-5-(SUBSTITUTED HETEROCYCLYL)-1,2,4-TRIAZOLE COMPOUNDS

RELATED APPLICATION

This application claims priority from U.S. Provisional Patent Application Ser. No. 60/105,354, filed Oct. 23, 1998.

FIELD OF THE INVENTION

This invention provides new compounds that are useful as insecticides and acaricides, new synthetic procedures and intermediates for preparing the compounds, pesticide compositions containing the compounds, and methods of controlling insects and mites using the compounds.

BACKGROUND OF THE INVENTION

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore a need exists for new insecticides and acaricides, and particularly for compounds that have new or atypical modes of action.

A number of 3,5-diphenyl-1H-1,2,4-triazole derivatives have been described in the literature as having acaricidal activity. U.S. Pat. No. 5,482,951; JP 8092224, EP572142, JP 08283261. To applicants knowledge, however, none of these compounds has become a commercial product. Nitro furanyl triazoles are described by L. E. Benjamin and H. R. Snyder as antimicrobials (*J. Heterocyclic Chem.* 1976, 13, 1115) and by others as antibacterials (*J. Med. Chem.* 1973, 16(4), 312–319; *J. Med. Chem.* 1974, 17(7), 756–758). The present invention provides novel compounds with commercial level activity against mites and insects.

SUMMARY OF THE INVENTION

This invention provides novel compounds especially useful for the control of insects and mites.

More specifically, the invention provides novel insecticidally active compounds of the formula (1)

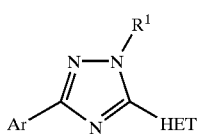

(1)

wherein
Ar is substituted phenyl;
$R^1$ is lower alkyl, haloalkyl, lower alkenyl, lower alkynyl, or alkoxyalkyl;
HET is a group selected from

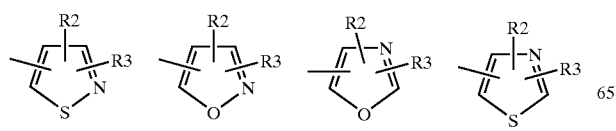

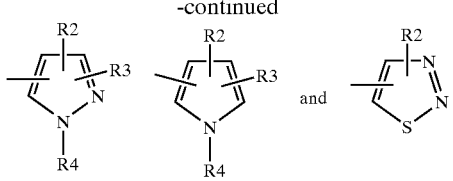

$R^2$ is selected from H, halo, lower alkyl, ($C_7$–$C_{21}$) straight chain alkyl, hydroxy, lower alkoxy, haloalkyl, haloalkoxy, alkoxyalkyl, alkoxyalkoxy, lower alkenyl, haloalkenyl, CN, $NO_2$, $CO_2R^6$, CON($R^6$)$_2$, ($C_3$–$C_6$) cycloalkyl, $S(O)_mR^6$, SCN, pyridyl, substituted pyridyl, isoxazolyl, substituted isoxazolyl, naphthyl, substituted naphthyl, phenyl, substituted phenyl, —($CH_2$)$_nR^6$, —CH=CH$R^6$, —C≡C$R^6$, —$CH_2OR^6$, —$CH_2SR^6$, —$CH_2NR^6R^6$, —$OCH_2R^6$, —$SCH_2R^6$, —$NR^6CH_2R^6$,

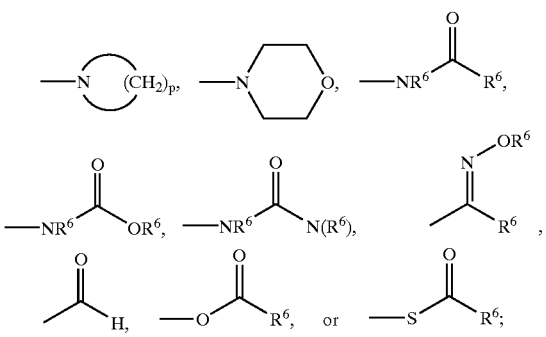

$R^3$ is H, halo, lower alkyl, lower alkoxy, haloalkyl, haloalkoxy, CN, $CO_2R^6$, CON($R^6$)$_2$, or $S(O)_m$ alkyl, or
$R^2$ and $R^3$ combine to form a 5 or 6 member saturated or unsaturated carbocyclic ring which may be substituted by 1 or 2 halo, lower alkyl, lower alkoxy or haloalkyl groups;
$R^4$ is H, lower alkyl, haloalkyl, lower alkenyl, lower alkynyl, phenyl, or substituted phenyl;
$R^6$ is H, lower alkyl, haloalkyl, lower alkenyl, lower alkynyl, phenyl, or substituted phenyl;
m is 0, 1, or 2; and
n is 1 or 2;
p is an integer from 2 to 6;
or a phytologically acceptable acid addition salt thereof.

Preferred compounds of formula (1) include the following classes:
(1) Compounds of formula (1) wherein Ar is a group of the formula

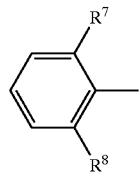

wherein $R^7$ and $R^8$ are independently H, Cl, F, methyl, halomethyl, methoxy, or halomethoxy.
(2) Compounds of class (1) wherein $R^7$ and $R^8$ are independently F or Cl.
(3) Compounds of class (3) wherein $R^7$ and $R^8$ are both F.

(4) Compounds of class (3) wherein $R^7$ and $R^8$ are both Cl.

(5) Compounds of class (3) wherein $R^7$ is F and $R^8$ is Cl.

(6) Compounds of formula (1), and particularly compounds of any one of classes (1) through (5) defined above, wherein
$R^1$ is methyl.

(7) Compounds of any one of classes (1) through (6) wherein HET is

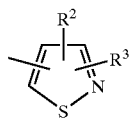

and $R^2$ and $R_3$ are as defined in formula (1).

(8) Compounds of any one of classes (1) through (6) wherein HET is

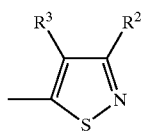

and $R^2$ and $R^3$ are as defined in formula (1).

(9) Compounds of any one of classes (1) through (6) wherein HET is

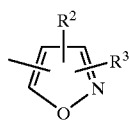

and $R^2$ and $R^3$ are as defined in formula (1).

(10) Compounds of any one of classes (1) through (6) wherein HET is

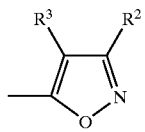

and $R^2$ and $R^3$ are as defined in formula (1).

(11) Compounds of any one of classes (1) through (6) wherein HET is

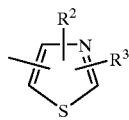

and $R^2$ and $R^3$ are as defined in formula (1).

(12) Compounds of any one of classes (1) through (6) wherein HET is

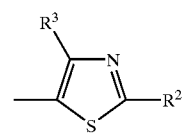

and $R^2$ and $R^3$ are as defined in formula (1).

(13) Compounds of any one of classes (1) through (6) wherein HET is

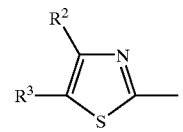

and $R^2$ and $R^3$ are as defined in formula (1).

(14) Compounds of any one of classes (1) through (6) wherein HET is

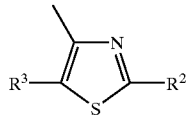

and $R^2$ and $R^3$ are as defined in formula (1).

(15) Compounds of any one of classes (1) through (6) wherein HET is

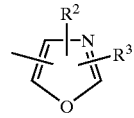

and $R^2$ and $R^3$ are as defined in formula (1).

(16) Compounds of any one of classes (1) through (6) wherein HET is

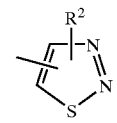

and $R^2$ is as defined in formula (1).

(17) Compounds of any one of classes (1) through (6) wherein HET is

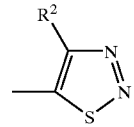

and $R^2$ is as defined in formula (1).

(18) Compounds of any one of classes (1) through (6) wherein HET is

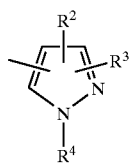

and $R^2$, $R^3$, and $R^4$ are as defined in formula (1).

(19) Compounds of any one of classes (1) through (6) wherein HET is

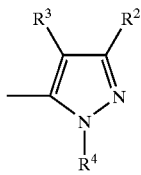

and $R^2$, $R^3$, and $R^4$ are as defined in formula (1).

(20) Compounds of any one of classes (1) through (6) wherein HET is

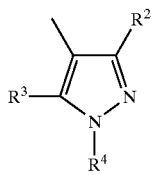

and $R^2$, $R^3$, and $R^4$ are as defined in formula (1).

(21) Compounds of any one of classes (1) through (6) wherein HET is

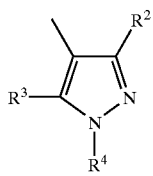

and $R^2$, $R^3$, and $R^4$ are as defined in formula (1).

(22) Compounds of any one of classes (1) through (6) wherein HET is

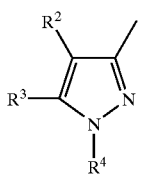

and $R^2$, $R^3$, and $R^4$ are as defined in formula (1).

(23) Compounds of any one of classes (1) through (6) herein HET is

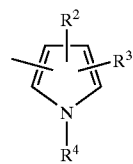

and $R^2$, $R^3$, and $R^4$ are as defined in formula (1).

(24) Compounds of any one of classes (1) through (6) wherein HET is

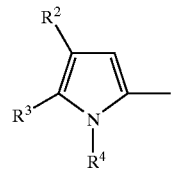

and $R^2$, $R^3$, and $R^4$ are as defined in formula (1).

The invention also provides new processes and intermediates for preparing compounds of formula (1) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to —O-lower alkyl.

The terms "halomethyl", "haloalkyl", and "haloalkenyl" refer to methyl, lower alkyl, and lower alkenyl groups substituted with one or more halo atoms.

The terms "halomethoxy" and "haloalkoxy" refer to methoxy and lower alkoxy groups substituted with one or more halo atoms.

The term "alkoxyalkyl" refers to a lower alkyl group substituted with a lower alkoxy group.

The term "alkoxyalkoxy" refers to a lower alkoxy group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

Unless otherwise indicated, when it is stated that a group may be substituted with one or more substituents selected from an identified class, it is intended that the substituents may be independently selected from the class.

Synthesis

Compounds of formula (1) can be prepared by the methods described in U.S. Pat. Nos. 5,380,944 and 5,284,860 (Production Methods 1, 2 and 3). Additional methods will be described hereinafter.

For example, compounds of Formula (1) can be prepared in accordance with the following reaction Scheme I:

Scheme I

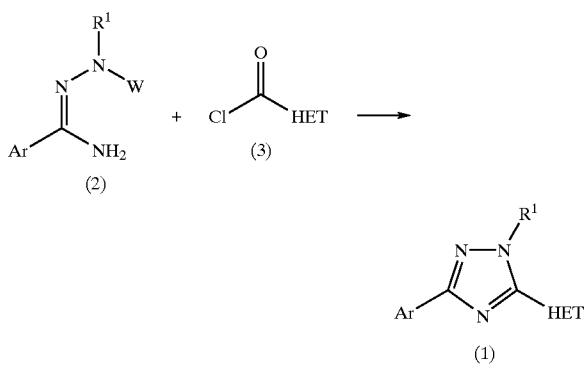

wherein Ar, HET and $R^1$, are as defined in formula (1) above, and W is a conventional amino protecting group. Examples of conventional amino protecting groups include, but are not limited to, the carbobenzyloxy group, tertiary alkoxycarbonyl groups, amides, phosphinyl and phosphoryl groups, and sulfenyl and sulfonyl groups. As illustrated in Scheme I, an N-protected amidrazone (2) is reacted with a compound of formula (3) in the presence of acid or base as catalyst. Intermediates of formulas (2) and (3) may be obtained by application of well known procedures.

For example, Scheme II illustrates preparation of the protected benzamidrazone starting material (2).

Scheme II

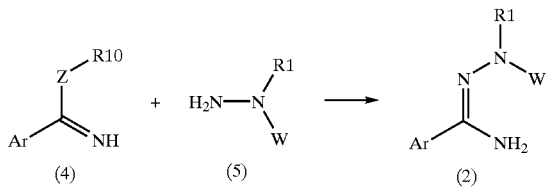

Benzimidate derivative (4), wherein Z is O or S, and $R^{10}$ is lower alkyl, is reacted with hydrazine derivative (5), wherein Ar, W, and $R^1$ are as defined above for Scheme I.

An example of an intermediate of formula (5) is N-methyl-N-t-butylcarboxyhydrazine. Its use in making regiospecific 1-alkyl[1,2,4]triazoles is found in *Chem. Ber.*, 1982, 115, 2807–2818. The production of benzimide compounds is well known. An example is disclosed in *Synth. Commun.*, 1983, 13, 753.

Another aspect of the invention is a new method for preparing compounds of formula (1) as illustrated in Scheme III.

Scheme III

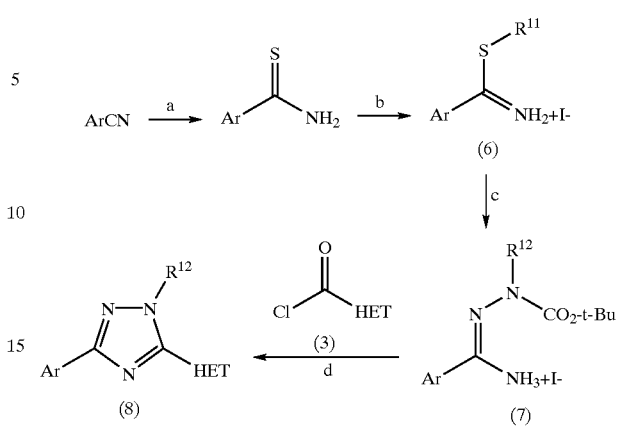

In Scheme III, Ar and HET are as defined in formula (1), $R^{11}$ is lower alkyl, preferably methyl, and $R^{12}$ is lower alkyl, preferably methyl.

As illustrated in step a of Scheme III, a substituted benzonitrile is reacted with triethylamine, sodium sulfide hydrate, and hydrochloric acid in pyridine at room temperature to give the substituted benzenethioamide.

In step b of Scheme III the substituted benzenethioamide is reacted with lower alkyl idodide, e.g. iodomethane, in acetone to provide an S-(lower alkyl)thio-substitutedbenzimidinium iodide of formula (6). Acetone is the preferred solvent, however other polar aprotic solvents such as DMF or THF can be used.

In step c of Scheme III the S-(lower alkyl)thio-substitutedbenzimidinium iodide is reacted with an N-t-butoxycarbonyl-N-(lower alkyl)hydrazine to provide the amidrazone of formula (7). The reaction is carried out in methanol or ethanol, preferably methanol, at a temperature of 0° C. to the boiling point of the solvent.

In step d of Scheme III, the amidrazone of formula (7) is reacted with an acid chloride of formula (3) in a nonreactive organic solvent such as benzene, toluene, xylenes, chloroform, dichloromethane, or 1,2-dichloroethane, at a temperature in the range from 0° C. to the boiling point of the solvent.

The process of Scheme III uses milder conditions than previously published processes, and therefore allows thermally sensitive heterocycles to be used. Higher yields are also provided.

EXAMPLE 1

The following steps illustrate preparation of the amidrazone of formula (7a)

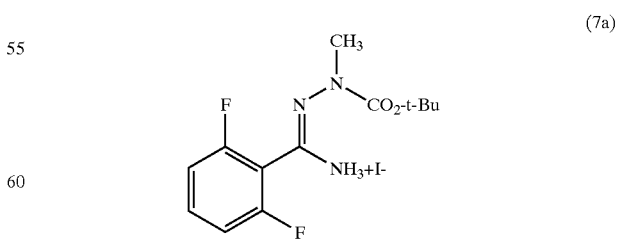

A. 2,6-Difluorobenzenethioamide (step a)

Into a 3 L three necked round bottom flask equipped with a mechanical stirrer, dry ice condenser, dropping funnel, and outlet to a trap filled with bleach was added pyridine (550 mL), 2,6-difluorobenzonitrile (208 g, 1.50 mol), triethylamine (202 g, 279 mL, 2.0 mol), and sodium sulfide hydrate (521 g, 2.17 mol, broken into pieces small enough to fit into the flask). The temperature of the stirred mixture was lowered to approximately 5° C. and to the slurry was added dropwise concentrated hydrochloric acid (143 g, 288 mL, 3.99 mol). An exotherm was noted and the rate of addition of the hydrochloric acid was such that the temperature of the reaction mixture did not exceed 25° C. for a total addition time of 75 min. The cooling bath was removed and the slurry was allowed to warm to RT and to stir over night. The mixture was poured into water (2 L) and was extracted with ether (3×500 mL). The ether layer was washed with dilute sulfuric acid, water, brine, dried (MgSO$_4$), and the solvent removed in vacuo to give 232 grams of crude product. The starting material was removed from the product via bulb-to bulb distillation to give 197 g (76%) of 2,6-difluorobenzenethioamide. This material was used without further purification.

B. S-Methylthio-2,6-difluorobenzamidinium iodide (step b)

Into a 3 L three necked flask equipped with a mechanical stirrer and dropping funnel was added acetone (1150 mL) and 2,6-difluorobenzenethioamide (197 g, 1.14 mol). The temperature of the stirred solution was lowered to approximately 5° C. and iodomethane (161 g, 70.6 mL, 1.14 mol) was added dropwise. The ice bath was removed and the slurry was allowed to stir over night. The resulting yellow solids were removed via filtration and washed with ether to obtain 223 grams. An additional portion of material was obtained from the filtrate by removal of the solvent in vacuo. Ether was added to the residue and the resulting solids removed via filtration to obtain an additional 57 grams of material. The combined solids totaled 280 g (77.9% yield) of S-methylthio-2,6-difluoro-benzimidinium iodide: mp 168–169° C.; $^1$H NMR (DMSO-d$_6$) δ7.7 (m, 1H), 7.4 (m, 2H), 2.7 (s, 3H).

C. N-tert-Butoxycarbonyl-N-methylhydrazine (step c)

Into a 1 L three necked round bottom flask equipped with a mechanical stirrer and dropping funnel was added methyl hydrazine (42.2 g, 0.916 mol) and THF (100 mL). The temperature of the mixture was cooled to 5° C. and a solution of di-tert-butyl dicarbonate (100 g, 0.458 mol) dissolved in THF (150 mL) was added dropwise. The cooling bath was removed and the mixture was stirred at RT overnight. The liquid was decanted from a gummy precipitate and the solvent removed in vacuo to give approximately 70 grams of a clear liquid. The gummy precipitate was partitioned between methylene chloride and water. The methylene chloride was washed with brine, dried (Na$_2$SO$_4$) and the solvent removed in vacuo. The resulting residue was combined with that from the previous evaporation and distilled at approximately 20 mm Hg (bp 77–78° C.) to give 40.2 g (60% yield) of N-tert-butoxycarbonyl-N-methylhydrazine: $^1$H NMR (CDCl$_3$) δ4.1(s, b, 2H), 3.05 (s, 3H), 1.5 (s, 9H).

D. Amidrazone of formula (7a)

Into a 1 L round bottom flask equipped with a mechanical stirrer, dropping funnel, and outlet to a trap filled with bleach, was added S-methyl-2,6-difluorobenziminium iodide (63.8 g, 0.202 mol) and methanol (180 mL). To the stirred solution was added dropwise N-tert-butoxycarbonyl-N-methylhydrazine (29.6 g. 0.202 mol). The solution was allowed to stir overnight and the methanol was removed in vacuo. The residue was triturated with ether and the solids removed via filtration to give 66.3 grams (79.0% yield) of the amidrazone of formula (2a): mp 172–173° C. (dec); $^1$H NMR (DMSO-d$_6$) δ12.3 (s, b, 1H), 10.4 (d, b, 2H), 7.9 (m, 1H), 7.4 (m, 2H), 3.1 (s, 3H), 1.5 (s, 9H).

Heterocyclic carboxylic acid derivatives of the formula (3) are prepared using conventional methods, as illustrated hereinafter.

Isothiazoles

The isothiazole carboxylic acid intermediates used in the following examples were prepared by the procedure shown in Scheme IV. Reaction of an arylacetonitrile, for example benzylcyanide, with sodium hydroxide followed by isoamylnitrite gives the oximino derivative. Reaction of the sodium salt of the oximino derivative with p-toluensulfonyl chloride give the tosylate ester. Reaction of the ester with thioglycoalte esters, in the presence of base yields the alkyl 3-aryl-4-amino-5-isothiazolecarboxylate. See J. R. Beck, R. P. Gajewski and R. E. Hackler, U.S. Pat. No. 4,544,752 (1985) and U.S. Pat. No. 4,346,094 (1982). The amino group of the isothiazole can the be transformed into a halogen via diazotization chemistry. See J. R. Beck, R. P. Gajewski, *J. Heterocyclic Chem*, 24, 243, 1987. The ester can then be hydrolyzed to the carboxylic acid with sodium hydroxide in dioxane/water.

Scheme IV

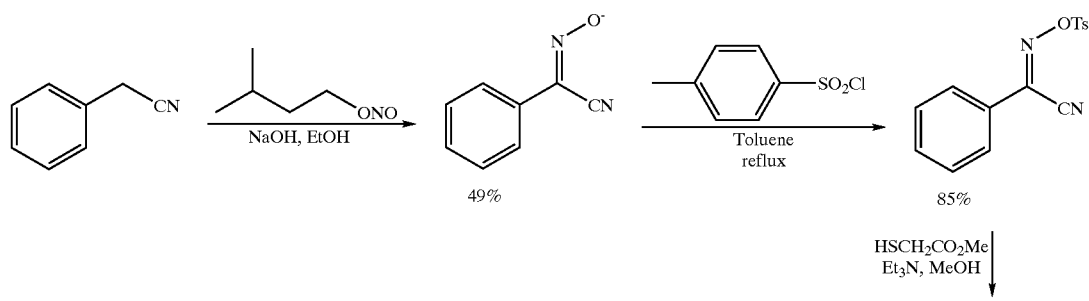

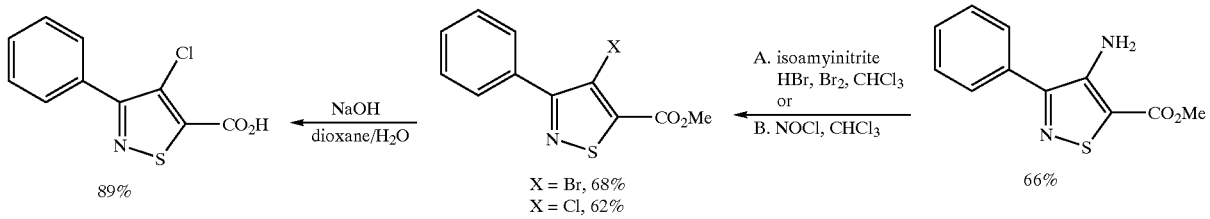

X = Br, 68%
X = Cl, 62%

EXAMPLE 2

A. Phenylglyoxylonitrile oxime, sodium salt

Isoamyl nitrite (32 mL, 0.24 mol) in 30 mL of ethanol was added dropwise to a mechanically stirred solution of benzyl cyanide (23 mL, 0.20 mol) and sodium hydroxide (8.0 g, 0.20 mol) in 100 mL of ethanol, under $N_2$, while cooling in an ice bath. The temperature was maintained at 10–20° C. throughout the addition. Once the addition was complete, the mixture was allowed to warm to room temperature. After stirring at room temperature for two hours, the reaction was diluted with $Et_2O$ (~200 mL) and the resultant precipitate was removed by vacuum filtration, washing with $Et_2O$. The solid was air dried and then vacuum oven dried (70–80° C.) to give 16.45 g (49% yield) of the desired product as a light yellow solid: mp 287–288° C. (decomp.); $^1H$ NMR (DMSO) δ7.58–7.55 (m, 2H), 7.28–7.22 (m, 2H), 7.07–7.02 (m, 1H).

B. α-(p-Toluenesulfonyloxyimino)phenylacetonitrile

A mixture of the oxime salt (16.19 g, 96 mmol) and p-toluenesulfonyl chloride (18.30 g, 96 mmol) in 125 mL of toluene was heated to reflux. After refluxing for two hours the reaction was allowed to cool, diluted with EtOAc (200 mL) and washed with $H_2O$ (1×100 mL) and saturated sodium chloride (1×100 mL). The organic phase was dried over anhydrous $MgSO_4$, filtered and concentrated to give 24.37 g (85% yield) of the desired product as light yellow flakes: mp 131–132° C.; $^1H$ NMR (CDCl$_3$) δ7.97–7.94 (m, 2H), 7.82–7.78 (m, 2H), 7.61–7.55 (m, 1H), 7.52–7.39 (m, 4H), 2.47 (s, 3H).

C. Ethyl 3-Phenyl-4-amino-5-isothiazolecarboylxate

Triethylamine (22 mL, 159 mmol) was added dropwise to a mechanically stirred mixture of the tosylate (23.92 g, 79.6 mmol) and methyl thioglycolate (8.5 mL, 95.5 mmol) in 200 mL of methanol at such a rate to keep the temperature <45° C. Once the addition was complete, the mixture was allowed to stir at room temperature. After ~2.5 hours the reaction was cooled (precipitate formed upon cooling) and treated with 100 mL of ice/$H_2O$. The resultant solid was removed via vacuum filtration, washing with $H_2O$. The solid was air dried for to give 13.88 g of an orange-yellow solid. Recrystallization from hexane/ethyl acetate and vacuum oven drying (70–80° C.) gave 12.31 g (66% yield) of the desired product as beige needles: mp 115–117° C.; $^1H$ NMR (CDCl$_3$) δ7.73–7.70 (m, 2H), 7.53–7.46 (m, 3H), 5.42 (bs, 2H), 3.91 (s, 3H).

D. Ethyl 3-Phenyl-4-bromo-5-isothiazolecarboylxate

Anhydrous HBr was bubbled into a solution of the aminoisothizole of Example 2C (6.70 g, 28.6 mmol) in 100 mL of CHCl$_3$, while cooling in an ice bath, for 5–10 minutes. The solution was then treated with bromine (5–6 mL) followed by the dropwise addition of isoamylnitrite (5.8 mL, 42.9 mmol). The resultant mixture was allowed to warm to room temperature and then heated to reflux. After refluxing for 15–20 minutes, the reaction was allowed to cool, treated with silica gel and then filtered, washing with CH$_2$Cl$_2$. The filtrate was concentrated in vacuo to give 9.29 g of a dirty yellow solid. Recrystallization from ethanol and vacuum oven drying (60–70° C.) gave 5.76 g (68% yield) of the desired product as light yellow flakes: mp 120–121° C.; $^1H$ NMR (CDCl$_3$) δ7.81–7.77 (m, 2H), 7.51–7.48 (m, 3H), 3.99 (s, 3H).

E. Ethyl 3-Phenyl-4-chloro-5-isothiazolecarboylxate

Nitrosyl chloride was generated by the dropwise addition of a solution of sodium nitrite (17.25 g, 0.25 mol) in 25 mL of $H_2O$ into 100 mL of concentrated HCl (1.2 mol) in a apparatus similar to that described in *Inorganic Synthesis*, 1953, 4, 48.

The nitrosyl chloride was allowed to bubble into a solution of the aminoisothiazole of Example 2C(5.0 g, 21.3 mmol) in 50 mL of CHCl$_3$, while cooling in an ice bath. Once the formation of nitrosyl chloride was complete the reaction mixture was allowed to warm to room temperature and then heated to reflux. After refluxing for 5 minutes, the reaction was allowed to cool, treated with silica gel and then filtered, washing with CH$_2$Cl$_2$. The filtrate was concentrated in vacuo to give 5.16 g of an orange solid. Recrystallization from ethanol and vacuum oven drying (60–70° C.) gave 3.37 g (62% yield) of the desired product as light yellow flakes: mp 101–102° C.; $^1H$ NMR (CDCl$_3$) δ7.86–8.83 (m, 2H), 7.51–7.47 (m, 3H), 3.99 (s, 3H).

F. 3-Phenyl-4-chloro-5-isothiazolecarboylic acid

A mixture of the ester of Example 2E(3.19 g, 12.6 mmol) in 10 mL of dioxane and 10 mL of 2N NaOH was stirred at room temperature. After stirring for 90 minutes TLC analysis indicated that all of the ester had been consumed. The reaction mixture was diluted with $H_2O$ (20 mL) and washed with $Et_2O$ (2×40 mL). The aqueous phase was acidified with concentrated HCl and extracted with ethyl acetate (3×50 mL). The combined ethyl acetate extracts were washed with saturated sodium chloride (1×50 mL), dried over anhydrous MgSO$_4$, filtered and concentrated in vacuo to give 2.69 g (89% yield) of the desired product as a white solid: mp 196–197° C.; $^1H$ NMR (DMSO-d$_6$) δ14.7–14.3 (bs, 1H), 7.81–7.77 (m, 2H), 7.56–7.54 (m, 3H).

1,2,3-Thiadiazoles

The 1,2,3-thiadiazolecarboxylic acid intermediates used in the following examples can be prepared according to literature procedures (*J.Chem. Soc.*, 1968, 46, 1057).

Thiazole intermediates

Method A

The 2-alky-5-arylthiazole-2-carboxylic acid derivatives were prepared by the route shown in Scheme V. Treatment of the benzoyl acetate with sufluryl chloride gave the intermediate 2-chloro-3-ketoester, which was cyclized with thioacetamide to give the desired thiazole ester derivative. The ester could then be transformed to the carboxylic acid as described above in Example 2F.

Scheme V

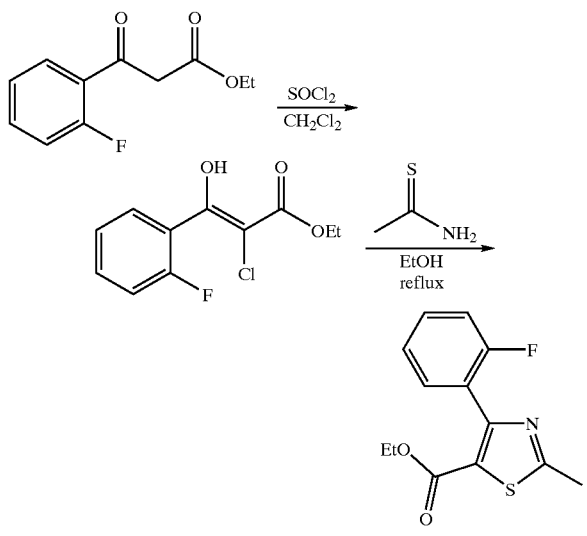

EXAMPLE 3

A. Ethyl 2-chloro-2-(2-fluorobenzoyl)acetate

Sulfuryl chloride (4.25 g, 32 mmol) was added dropwise to a solution ethyl 2-(2-flurobenzoyl)acetate (6.30 g, 30 mmol) in $CH_2Cl_2$ (75 mL) at room temperature. No exotherm was observed after 30 minutes, only slight bubbling. After stirring overnight TLC analysis indicated that all of the starting material had been consumed. The reaction mixture was treated with $H_2O$ (100 mL). The resultant mixture was stirred for 20 minutes and the phases were separated. The organic phase was washed with $H_2O$ (2×100 mL), dried over anhydrous $MgSO_4$, filtered and concentrated in vacuo to give 6.85 g (93% yield) of the desired product as an orange oil: $^1H$ NMR ($CDCl_3$) δ8.0–7.9 (m, 1H), 7.6–7.5 (m, 1H), 7.3–7.1 (m, 2H), 5.6 (s, 1H), 4.25 (q, 2H), 1.25 (t, 3H).

B. Ethyl 2-methyl-4-(2-fluorophenyl)-5-thiazole-carboxylate

A mixture of the 2-chloro-3-ketoester (3.50 g, 14.3 mmol) and thioacetamide (1.07 g, 14.3 mmol) in absolute ethanol (100 mL) was heated to reflux. After refluxing over the weekend (~3 days), TLC analysis showed one major product and only a trace amount of the starting material present. The reaction mixture was allowed to cool to room temperature, stripped to one half the original volume and then diluted with $H_2O$ (200 mL). The solution was made basic with 2N NaOH and the remaining ethanol removed. The aqueous phase was extracted with ethyl acetate (150 mL). The organic phase was washed with $H_2O$ (2×100 mL), dried over anhydrous $MgSO_4$, filtered and concentrated onto silica gel. This was chromatographed over silica gel (300 g, MPLC). Eluting with a serial dilution of hexanes to 90% heaxanes/ 10% ethyl acetate. Isolation of the major product gave 1.95 g (51% yield) of the desired product as a yellow oil: $^1H$ NMR ($CDCl_3$) δ7.6–7.5 (m, 1H), 7.4–7.3 (m, 1H), 7.25–7.05 (m, 2H), 4.2 (q, 2H), 2.7 (s, 3H), 1.2 (t, 3H).

Method B

The second general route to the desired thiazole derivative is shown in Scheme VI (J. Het. Chem., 1985, 22, 1621). The cyclization of ethyl 2-chloroacetoacetate with thiourea gave the 2-aminothiazole. The desired 2-halothiazole could then be prepared via diazotization of the aminothiazole. The ester could then be transformed to the carboxylic acid as described above in Example 2F.

Scheme VI

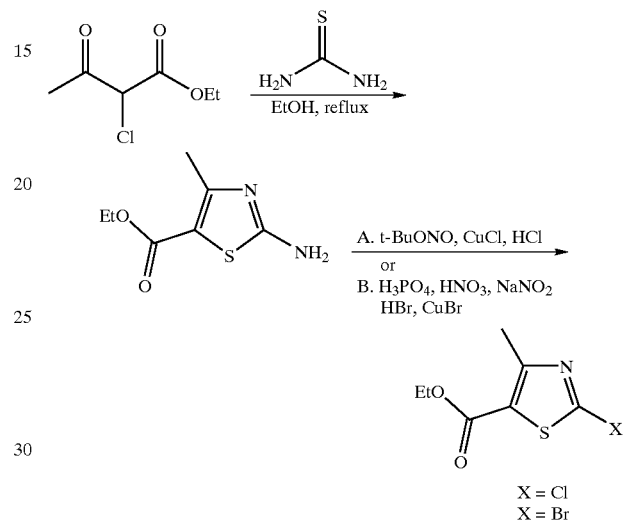

EXAMPLE 4

A. Ethyl 2-Amino-4-methyl-5-thiazolecarboxylate

A mixture of ethyl 2-chloroacetoacetate (50 g, 0.30 mol, Aldrich) and thiourea (45.6 g, 0.60 mol) in 400 mL of absolute ethanol was heated to reflux. After refluxing overnight the reaction mixture was allowed to cool to room temperature and then concentrated to half the original volume in vacuo. The remaining ethanol solution was poured into $H_2O$ (1 L) and made basic (pH 10) with 2N NaOH. An off-white solid precipitated immediately. The mixture was stirred for 10 minutes and then the solid was removed by vacuum filtration and dried to give 54.75 g (98% yield) of the desired product as a white solid: $^1H$ NMR ($CDCl_3$) δ5.5 (bs, 2H), 4.25 (q, 2H), 2.5 (s, 3H), 1.35 (t, 3H).

B. Ethyl 2-chloro-4-methyl-5-thiazolecarboxylate

To a mixture of t-butyl nitrite (8.30 g, 80 mmol), cuprous chloride (6.38 g, 65 mmol) in 400 mL of acetonitrile was added Ethyl 2-Amino-4-methyl-5-thiazole-carboxylate (10 g, 54 mmol) in one portion. The thiazole dissolved after 25 minutes, and the reaction was allowed to stir at room temperature for 2 hours. The temperature was then increased to 66° C. for one hour. The solution was gradually allowed to cool to room temperature and filtered. The filtrate was poured into 400 mL of 6N HCl (the solution began fizzing). The solution was stirred for 20 minutes at which time TLC analysis showed that all of the starting material had been consumed and one product formed. The aqueous mixture was diluted with 700 mL of $H_2O$ and then extracted with ethyl acetate (4×400 mL). The ethyl acetate fractions were dried over anhydrous $MgSO_4$, filtered and concentrated in vacuo to give 10.45 g (94% yield) of a reddish oil which crystallized to a reddish-orange solid: ¹H NMR (CDCl₃) δ4.35 (q, 2H), 2.7 (s, 3H), 1.35 (t, 3H).

C. Ethyl 2-Bromo-4-methyl-5-thiazolecarboxylate

A solution of sodium nitrite (8.56 g, 124 mmol) in 20 mL of H₂O was added over a 30 minute period to a mixture of the aminothiazole (7.44 g, 40 mmol), 85% phosphoric acid (50 mL) and 70% nitric acid (25 mL) at −10° C. The mixture began to bubble immediately and an exotherm was observed. A CO₂/acetone bath was used to maintain the temperature at −10° C. throughout the addition. An orange precipitate formed and the mixture became very difficult to stir. Once the addition was complete, the mixture was allowed to warm to room temperature and stirred for ~20 minutes. The reaction mixture was then poured into a mixture of hydrobromic acid (20 mL) and cuprous bromide (5.74 g, 40 mmol). After vigorous gas evolution, the mixture was diluted with H₂O (650 mL) and filtered to yield a brown solid. The solid was dissolved in ethyl acetate and concentrated onto ~100 g of silica gel and chromatographed over silica gel, eluting with a serial dilution of hexane to 90% hexane/10% ethyl acetate. Isolation of the major product gave 1.92 g (19% yield) of the desired product as a yellow solid: mp 63–65° C.; ¹H NMR (CDCl₃) δ4.35 (q, 2H), 2.7 (t, 3H), 1.35 (t, 3H).

Pyrrole Intermediates

Two well known routes to generate pyrroles include the Hantzsch synthesis (*Rec. Trav. Chem.*, 1979, 98, 437) and the Knorr synthesis (Die Chemnie Des Pyrroles, Vol. 1, Akademische verlagsgesellschaft, Leipzig, 1934, pp 3–5). The dibromo analog was prepared as described in Example 5.

EXAMPLE 5

4,5-Dibromo-1-methyl-2-pyrrolecarboxylic acid

A solution of 1-methyl-2-pyrrolecarboxylic acid (0.80 g, 6.4 mmol) and bromine (990 μL, 19.2 mmol) in 10 mL of acetic acid was allowed to stir at room temperature. After three hours the precipitate that had formed was removed by vacuum filtration, washed with H₂O and vacuum dried to give 0.94 g (52% yield) of the desired product as a white solid. The intermediate was used without further purification.

Pyrazole Intermediates

The pyrazole intermediates were from commercial sources or readily synthesized according to literature procedures. See, for example, *J. Org. Chem.*, 1966, 31, 1878; *J. Soc. Chem. France*, 1966, 293. Synthetic routes to pyrazoles have also been reviewed (*Advances in Heterocyclic Chemistry*, Vol. 6, A. R. Kratritzky and A. J. Boulton, Eds., Academic Press, New York, 1966, pp 347–426; *Pyrazole, Pyrazolines, Indazoles and Condensed Rings*, R. H. Wiley, Ed., Interscience, New York, 1967, pp 10–64). The pyrazole intermediates can be alkylated using the general procedure described below. This results in a mixture of isomers which can be readily separated via chromatography and the ester converted to the carboxylic acid as described above in Example 2F.

EXAMPLE 6

Alkylation of Ethyl 3-methyl-5-pyrazolecarboxylate

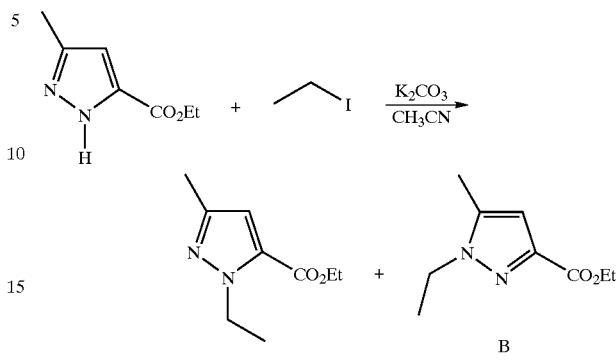

Ethyl iodide (2.0 mL, 25 mmol) was added to a mixture of ethyl 3-methylpyrazole-5-carboxylate (3.85 g, 25 mmol) and potassium carbonate (3.80 g, 27.5 mmol) in 25 mL of acetonitrile and the resultant mixture was heated to reflux. After refluxing over the weekend (72 h) GC analysis showed <5% starting material remaining. The reaction mixture was poured into H₂O (50 mL) and extracted with Et₂O (3×50 mL). The combined organic extracts were washed with H₂O (1×50 mL), saturated sodium chloride (1×50 mL), dried over anhydrous MgSO₄, filtered and concentrated in vacuo to give 4.12 g of a faint yellow oil. This was chromatographed on silica gel (MPLC), eluting with 70% hexane/30% ethyl acetate. The following were isolated:

Ethyl 1-Ethyl-3-methyl-5-pyrazolecarboxylate (A)

g (37% yield), colorless oil: ¹H NMR (CDCl₃) 66.60 (s, 1H), 4.53 (q, 2H, J=7.2 Hz), 4.32 (q, 2H, J=7.5 Hz), 2.27 (s, 3H), 1.41 (t, 3H, J=7.4 Hz), 1.37 (t, 3H, J=7.2 Hz).

Ethyl 1-Ethyl-5-methyl-3-pyrazolecarboxylate (B)

1.72 g (38% yield), colorless oil: ¹H NMR (CDCl₃) δ6.55 (s, 1H), 4.39 (q, 2H, J=6.9 Hz), 4.18 (q, 2H, J=7.2 Hz), 2.30 (s, 3H), 1.43 (t, 3H, J=7.2 Hz), 1.38 (t, 3H, J=7.2 Hz).

Isoxazole Intermediates

The isoxazole intermediates can be prepared according to literature procedures(Chemistry of Heterocyclic Compounds, A Weissberger, Ed., Vol. 17, Wiley-Interscience, New York, 1976, 162). An example of a general route used for the synthesis of isoxazoles intermediates in given in Scheme VII.

Scheme VII

17

-continued

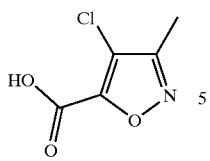

EXAMPLE 7

A. Ethyl 3-chloro-2,4-dioxovalerate

A solution of sulfuryl chloride (7.08 g, 52 mmol) in 15 mL of $CH_2Cl_2$ was added dropwise to a solution of ethyl 2,4-dioxovalerate (7.91 g, 40 mmol) in 125 ml of $CH_2Cl_2$ at room temperature. After three hours TLC analysis indicated that all of the starting material had been consumed. The reaction mixture was washed with $H_2O$ (2×100 mL), dried over anhydrous $MgSO_4$, filtered and concentrated in vacuo to give 7.84 g (81% yield) of the desired product as and orange oil: $^1H$ NMR ($CDCl_3$) δ14.4 (bs, 1H), 5.4 (s, 1H), 4.4–4.3 (m, 4H), 2.5 (s, 3H), 2.4 (s, 3H), 1.4–1.35 (s, 6H) for a 1:1 mixture of tautomers.

B. 3-Methyl-4-chloro-5-isoxazolecarboxylic acid

A solution of ethyl 3-chloro-2,4-dioxovalerate (3.0 g, 15.6 mmol) and hydroxylamine hydrochloride (1.08 g, 15.6 mmol) in a mixture of 1.5 mL of $H_2O$ and 1 mL of $CH_3OH$ was heated to reflux. After four hours TLC analysis indicated that all of the starting material had been consumed. Sodium hydroxide (0.31 g, 7.8 mmol) was added to the hot solution. After four hours the mixture was allowed to cool to room temperature and concentrated in vacuo. The residue was taken up in a 1:1 mixture to ethyl acetate/$H_2O$. The aqueous layer was made basic with 2N NaOH and separated. The aqueous layer was then acidified with 2M HCl and extracted with ethyl acetate (125 mL). The ethyl acetate extract was washed with $H_2O$ (2×100 mL), dried over anhydrous $MgSO_4$, filtered and concentrated in vacuo to give 600 mg (24% yield) of the desired product a gummy tan solid: $^1H$ NMR ($CDCl_3$) δ8.8 (bs, 1H), 2.3 (s, 3H).

Oxazole Intermediates

The numerous routes to oxazoles have been reviewed (*Chem. Rev.*, 1975, 75, 389).

The following are Examples of final products of the general formula (8).

EXAMPLE 8

3-(2,6-Diflurophenyl)-5-(3-phenyl-4-chloroisothiazo-5-yl)-1-methyl[1,2,4]triazole A mixture of 3-chloro-5-phenylisothiazole-2-carboxylic acid (1.00 g, 4.2 mmol) and 7 mL of thionyl chloride was heated to reflux. After refluxing for 90 min, the excess thionyl chloride was removed in vacuo. The crude acid chloride was taken up in toluene (10 mL), treated with the amidrazone of Example 1 (1.74 g, 4.2 mmol) and a catalytic amount of p-toluenesulfonic acid. The resultant mixture was heated to reflux. After refluxing for 3.5 hours, the reaction mixture was allowed to cool, poured into 1N NaOH (50 mL) and extracted with ethyl acetate (3×50 mL). The combined organic was washed with $H_2O$ (1×50 mL), saturated NaCl (1×50 mL), dried over anhydrous $MgSO_4$, filtered and concentrated in vacuo to give 1.52 g of a brown oil. This was chromatographed on silica gel (MPLC), eluting with 80% hexane/20% ethyl acetate. Isolation of the major product gave 0.809 g (50% yield) of the desired product as a tan solid: mp 122–123° C.; $^1H$ NMR ($CDCl_3$) δ7.94–7.90 (m, 2H), 7.54–7.39 (m, 4H), 7.08–7.02 (m, 2H), 4.10 (s, 3H).

EXAMPLE 9

3-(2,6-Diflurophenyl)-5-(4-bromo-1-ethyl-3-methylpyrazo-5-yl)-1-methyl[1,2,4]triazole A mixture of 4-bromo-1-ethyl-3-methylpyrazole-5-carbonyl chloride (1.05 g, 4.2 mmol) the amidrazone of Example 1 (1.45 g, 3.5 mmol) and a catalytic amount of p-toluenesulfonic acid was taken up in toluene (10 mL). The resultant mixture was heated to reflux. After refluxing for 6 hours, the reaction mixture was allowed to cool, diluted with ethyl acetate (150 mL) and washed with 1N NaOH (50 mL), $H_2O$ (1×50 mL) and saturated NaCl (1×50 mL). The organic phase was dried over anhydrous $MgSO_4$, filtered and concentrated in vacuo to give 1.20 g of a dark yellow oil. This was chromatographed on silica gel (MPLC), eluting with 70% hexane/30% ethyl acetate. Isolation of the major product gave 0.458 g (34% yield) of the desired product as a light tan solid: mp 77–79° C.; $^1H$ NMR ($CDCl_3$) δ7.43–7.38 (m, 1H), 7.08–7.01 (m 2H), 4.21 (q, 2H), 4.02 (s, 3H), 2.33 (s, 3H), 1.38 (t, 3H).

EXAMPLE 10

3-(2,6-Diflurophenyl)-5-(4-chloro-3-methylisoxazol-5-yl)-1-methyl[1,2,4]triazole A solution of 4-chloro-3-methylisoxazole-5-carboxylic acid (0.50 g, 0.003 mmol) in $CH_2Cl_2$ (20 mL) was treated with thionyl chloride (5 mL) and the mixture was heated to reflux. After refluxing for 4 hours, the mixture was concentrated in vacuo. The crude acid chloride was taken up in toluene (25 mL), treated with the amidrazone of Example 1(1.28 g, 0.003 mmol) and heated to reflux. After refluxing for 4 hours the reaction mixture was allowed to cool to room temperature and stirred overnight. The reaction mixture was concentrated in vacuo. The residue was taken up in ethyl acetate (100 mL) and washed with $H_2O$ (2×100 ml). The organic layer was dried over anhydrous $MgSO_4$, filtered and concentrated in vacuo to give a dark "gum". This was chromatographed on silica gel (MPLC), eluting with a serial dilution of hexane to 20% ethyl acetate. Isolation of the product gave 0.520 g (56% yield) of the desired product as a yellow solid: mp 94–97° C.; $^1H$ NMR ($CDCl_3$) δ7.45–7.35 (m, 1H), 7.05–6.95 (m, 2H), 4.25 (s, 3H), 2.40 (s, 3H).

EXAMPLE 11

3-(2,6-Difluorophenyl)-5-(4-methyl-1,2,3-thiadiazo-5-yl)-1-methyl[1,2,4]triazole A mixture of the amidrazone of Example 1 (1.0 g, 2.4 mmol), 4-methyl-1,2,3-thiadiazole-5-carbonyl chloride (0.41 g, 2.5 mmol) and p-touleunesulfonic acid (0.3 g) in toluene was heated to reflux in a flask equipped with a Dean-Stark trap. After refluxing overnight the reaction mixture was allowed to cool and washed with 2N NaOH and $H_2O$. The organic phase was dried over anhydrous $MgSO_4$, filtered and concentrated in vacuo to give 0.5 g (71% yield) of the desired product as a yellow oil which solidified upon standing: mp 80–83° C.; $^1H$ NMR ($CDCl_3$) δ7.45–7.35 (m, 1H), 7.1–7.0 (m, 2H), 4.05 (s, 3H), 2.95 (s, 3H).

EXAMPLE 12

3-(2,6-Difluorophenyl)-5-[4-(2-fluorophenyl)-2-methylthiazo-5-yl]-1-methyl[1,2,4]triazole Thionyl chloride (5 mL) was added to a solution of 4-(2-fluorophenyl)-2-methyl-5-thiazolecarboxylic acid (0.3 g, 1.5 mmol) in CH$_2$Cl$_2$ (15 mL). The resultant mixture was heated to reflux for ~2.5 hours and then concentrated in vacuo. The crude acid chloride was taken up in toluene (25 mL) and treated with the amidrazone of Example 1(0.78 g, 1.9 mmol) and heated to reflux. After refluxing overnight the mixture was allowed to cool to room temperature and the solvent removed in vacuo. The resultant green "gum" was taken up in ethyl acetate (150 mL) and washed with H$_2$O (3×100 mL), dried over anhydrous MgSO$_4$ and filtered. Silica gel was added (50 mL) and the solvent removed in vacuo. The resultant material was chromatographed over silica gel (MPLC) eluting with a serial dilution of hexanes to 30% ethyl acetate. Isolation of the major product gave 190 mg (33% yield) of the desired product as a yellow solid: mp 138–141° C.; $^1$H NMR (CDCl$_3$) δ7.6–7.5 (m, 1H), 7.4–7.3 (m, 2H), 7.2–6.9 (m, 4H), 3.55 (s, 3H), 2.8 (s, 3H).

EXAMPLE 13

3-(2,6-Difluorophenyl)-5-(1-methylpyrrol-2-yl)-1-methyl[1,2,4]triazole

A mixture of 1-methylpyrrole-2-carboxylic acid (1.75 g, 14 mmol), thionyl chloride (3.0 mL, 41 mmol) and DMF (4 drops) in 1,2-dichloroethane (40 mL) was heated to reflux. After 5 hours and GC-MS analysis of an aliquot shot inot methanol showed the reaction to be complete. The reaction mixture was concentrated in vacuo. The crude acid chloride (1.0 g, 7 mmol) was combined with the amidrazone of Example 1(2.0 g, 7 mmol) in toluene (60 mL) and heated to reflux in a flask equipped with a Dean-Stark trap. After refluxing overnight. The crude reaction mixture was filtered through silica gel, rinsing with ethyl acetate. The crude material was chromatographed over silica gel (MPLC), eluting with 75% hexane/25% ethyl acetate. This resulted in impure material which was rechromatographed, eluting with CH$_2$Cl$_2$. This gave 84 mg (4% yield) of the desired product as a yellow oil:

EXAMPLE 14

3-(2,6-Difluorophenyl)-5-(4-methyloxazol-5-yl)-1-methyl[1,2,4]triazole

The amidrazone of Example 1(2.07 g, 5.0 mmol) was added in one portion to a solution of 4-methyl-5-oxazolecarbonyl chloride (0.73 g, 5.0 mmol) in 10 mL of toluene. The resultant mixture was heated to reflux along with a catalytic amount of p-toluenesulfonic acid. After refluxing for four hours the reaction mixture was allowed to cool, poured into 1N NaOH (50 mL) and extracted with ethyl acetate (3×50 mL). The combined organic extracts were washed with H$_2$O (1×50 mL), saturated sodium chloride (1×50 mL), dried over anhydrous MgSO$_4$, filtered and concentrated in vacuo to give 1.20 g of a yellow solid. This was chromatographed over silica gel (MPLC), eluting with 65% hexanes/35% ethyl acetate. Isolation of the major product gave 0.657 g (48% yield) of the desired product as a light tan solid: mp 113–115° C.; $^1$H NMR (CDCl$_3$) δ7.97 (s, 1H), 7.43–7.34 (m, 1H), 7.05–6.98 (m, 2H), 4.20 (s, 3H), 2.58 (s, 3H).

The invention also provides a new method for preparing compounds of formula (1A) as illustrated in Scheme VIII:

Scheme VIII

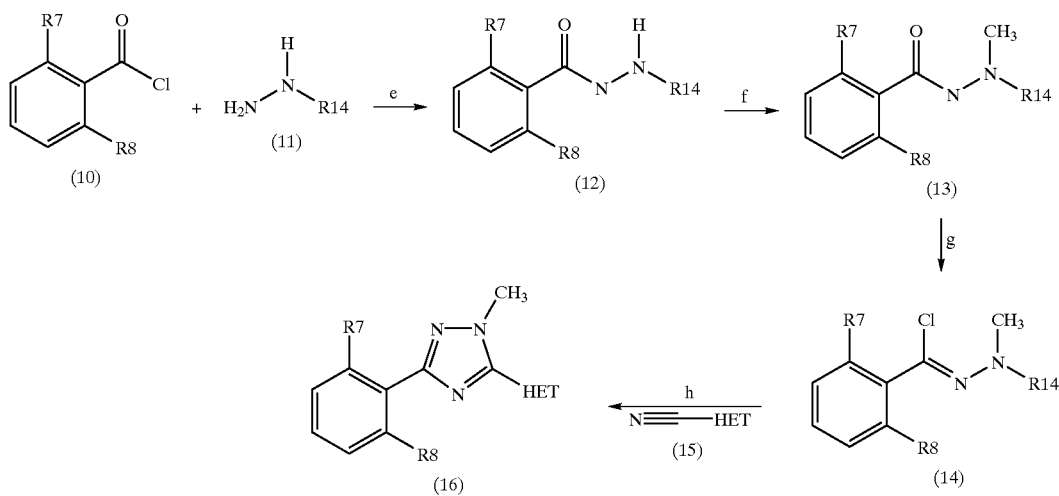

wherein R$^7$ and R$^8$ are independently H, Cl, F, methyl, halomethyl, methoxy, halomethoxy, HET is defined in formula (1) and R$^{14}$ is methanesulfonyl, benzenesulfonyl, or substituted benzenesulfonyl.

In step e, 2,6-disubstitutedbenzoylchloride (10) is reacted with a hydrazide of formula (11) (wherein R$^{14}$ is methanesulfonyl, benzenesulfonyl, or substituted benzenesulfonyl, i.e. p-Cl or p-CH$_3$ benzenesulfonyl) and triethylamine in THF to give the substituted benzhydrazone of formula (12).

In step f, the substitued benzhydrazone of formula (12) is reacted first with sodium hydride in N,N-dimethylformamide and then with iodomethane to produce the substituted hydrazine of formula (13).

In step g the substituted hydrazine of formula (13) is chlorinated using, e.g. PCl$_5$ to produce substituted benzylhydrazonoyl chloride of formula (14). The reaction is carried out in a non-reactive organic solvent such as dichloroethane.

In step h the substituted benzylhydrazonoyl chloride of formula (14) is reacted with a mixture of aluminum chloride and cyanoheterocycle of formula (15) in a solvent, e.g.

o-dichlorobenzene, to produce a 3-(2,6-substituted phenyl)-5-(substituted heteerocycle)-1-methyl[1,2,4]triazole of formula (16).

A detailed illustration of steps e–f of Scheme VIII is given in Example 15 hereinafter. Detailed illustrations of step h are given in Examples 18–22 hereinafter.

EXAMPLE 15

The following steps show preparation of the benzhyrazonoyl chloride of formula (14a)

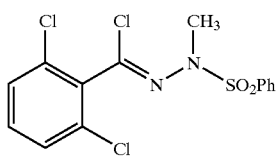

(14a)

A. 1-Benzenesulfonyl-2-(2,6-dichloro)benzhydrazone (step e)

Into a 1 L three necked round bottom flask equipped with a condenser, mechanical stirrer, thermometer, under an atmosphere of nitrogen, was added THF (500 mL), benzenesulfonyl hydrazide (41.1 g, 0.238 mol), and triethylamine (24.1 g, 33.2 mL, 0.238 mol). The resulting solution was cooled to −5° C. and 2,6-dichlorobenzoyl chloride (50.0 g, 34.2 mL, 0.238 mol) was added dropwise over a 55-min period and the temperature did not rise above 0° C. The reaction mixture was allowed to stir for 1 hr and then the cooling bath was removed and the reaction mixture was then stirred 21 hr at room temperature with monitoring via TLC and HPLC. Most of the solvent was removed in vacuo and the residue partitioned between methylene chloride (1000 mL) and water (2×200 mL). The organic layer was washed with saturated brine (250 mL), dried (Na$_2$SO$_4$), and the solvent removed in vacuo to give a white solid. The white solids were slurried in ether and were removed via filtration and dried in vacuo overnight to give 74.3 g (90.5% yield of 1-benzenesulfonyl-2-(2,6-dichlorobenz)hydrazone: mp 180–181° C.; TIC mass 345/347/349; $^1$H NMR (CDCl$_3$) δ8.05 (m, 2H), 7.9 (m, 1H), 7.5–7.7 (m, 4H), 7.3 (m, 3H).

B. 1-(2,6-dichloro)benzoyl-2-methyl-2-benzenesulfonyl hydrazine (step f)

In a 1 L three necked round bottom flask equipped with a mechanical stirrer, thermometer, and dropping funnel under an atmosphere of nitrogen a suspension of sodium hydride (8.49 g of 60% dispersion, 0.212 mol) was washed with hexanes (3 portions) and most of the hexane from the final wash was removed via suction. N,N-dimethylformamide (200 mL) was added and the temperature of the slurry lowered to −5° C. A solution of N-benzenesulfonyl-2,6-dichloro-benzhydrazone (73.3 g, 0.212 mol, in 300 mL of N,N-dimethylformamide) was added dropwise over a 120 min period at a rate such that the temperature did not rise above 3° C. and the rate of hydrogen evolution was maintained at a manageable rate. As the addition proceeded the mixture turned lemon yellow and thickened, but when the addition was completed the mixture was clear and easily stirred. The resulting mixture was stirred at 0° C. for 1 hr and the cooling bath removed and stirred for an additional 1 hr (temperature rose to 15° C.). The mixture was then cooled to −5° C. and iodomethane (30.0 g, 13.2 mL) was added dropwise at a rate such that the temperature did not rise above 0° C. The cooling bath was removed and the reaction mixture was allowed to warm to room temperature and to stir for 2 hr. The reaction mixture was diluted with brine (300 mL) and extracted with ethyl acetate. The organic layer was washed with saturated brine, dried (Na$_2$SO$_4$), and the solvent removed in vacuo to give crude material contaminated with N,N-dimethylformamide which was removed via vacuum pump. The crude mixture was crystallized in hexanes/ethyl acetate, the solids removed via filtration, and dried in vacuo to give 40.2 g. Solvent was removed from the filtrate to obtain an additional 21.4 g for a total of (80.9% yield) of 1-(2,6-dichlorobenzoyl)-2-methyl-2-benzenesulfonyl hydrazine: mp 177–178° C.; $^1$H NMR (CDCl$_3$) δ8.0 (m, 2H), 7.4–7.8 (m, 4H), 7.2 (m, 3H), 3.4 and 3.05 (two singlets combined for 3H).

C. N-(Benzenesulfonyl)-N-methyl-(2,6-dichlorobenz)hydrazonoyl chloride (step g)

Into a 1 L three necked round bottom flask equipped with a magnetic stirrer and condenser under an atmosphere of nitrogen was added N-benzenesulfonyl-N-methyl-2,6-dichlorobenzoyl hydrazine (35.9 g, 0.10 mol), 1,2-dichloroethane (500 mL), and phosphorus pentachloride (31.2 g, 0.15 mol). The temperature of the mixture was raised to the point of reflux and was allowed to stir for 30 min. The solvent was removed in vacuo and the residue dissolved in methylene chloride and carefully diluted with water. The organic phase was washed with water, brine, dried (Na$_2$SO$_4$) and the solvent removed in vacuo to give an oil which solidified when triturated with ethyl acetate/hexanes mixture to give 36.1 g (95.7% yield) N-benzenesulfonyl-N-methyl-2,6-dichlorobenzhydrazonoyl chloride as a white crystalline solid: mp 103–104° C.; $^1$H NMR (CDCl$_3$) δ7.9 (m, 2H), 7.4–7.7 (m, 3H), 7.2–7.4 (m, 3H), 3.1 (s, 3H).

N-Benzenesulfonyl-N-methyl-2-chloro-6-fluorobenzhydrazonoyl chloride was also made using the same procedure.

The cyanoheterocycles used in preparing the following compounds were commercially available or prepared from the carboxylic acids described above using the general route shown in Scheme IX for the synthesis of an isothiazolecarboxylic acid. The carboxylic acid were converted to the acid chlorides with thionyl chloride and then reacted with ammonia to give the corresponding amides. The amide could then be dehydrated by heating with phosphorus oxychloride to give the nitrile.

Scheme IX

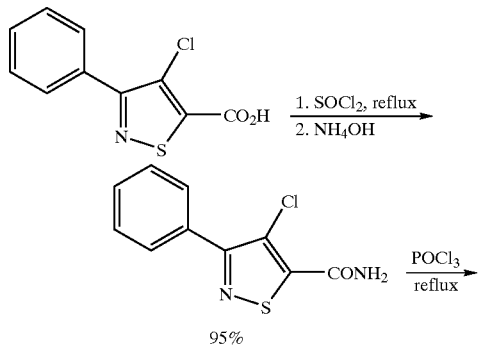

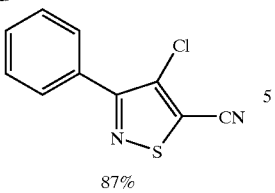

87%

A. 3-Phenyl-4-chloro-5-isothioazolecarboxamide

A mixture of 3-phenyl-4-chloro-5-isothiazolecarboxylic acid (1.57 g, 6.6 mmol) and 10 mL of thionyl chloride was heated to reflux. After refluxing for 90 minutes, the excess thionyl chloride was removed in vacuo. The crude acid chloride was treated with 10 mL of 30% aqueous ammonium hydroxide and the resultant mixture was warmed to 50° C. After 90 minutes at 50–60° C. the reaction was allowed to cool to room temperature. The solid was removed by vacuum filtration, washing with $H_2O$. The solid was air dried for several hours and then vacuum oven dried (60–70° C.) to give 1.502 g (95% yield) of the desired product as a white solid: mp 180° C.; $^1H$ NMR (CDCl$_3$) δ7.81–7.77 (m, 2H), 7.52–7.49 (m, 3H), 6.94 (bs, 1H), 6.35 (bs, 1H).

B. 3-Phenyl-4-chloro-5-isothioazolecarbonitrile

A mixture of 3-Phenyl-4-chloro-5-isothioazolecarboxamide (1.374 g, 5.8 mmol) and 5 mL of phosphorus oxychloride was heated to reflux. After refluxing for 60 minutes TLC analysis indicated that all of the amide starting material had been consumed. The reaction mixture was allowed to cool and then cautiously poured into $H_2O$ (50 mL). The aqueous phase was extracted with ethyl acetate (3×50 mL). The combined organic extracts were washed with $H_2O$ (1×50 mL), saturated sodium chloride (1×50 mL), dried over anhydrous MgSO$_4$, filtered and concentrated in vacuo to give 1.113 g (87% yield) of the desired product as a cream colored solid: mp 211–212° C.; $^1H$ NMR (CDCl$_3$) δ7.89–7.86 (m, 2H), 7.53–7.51 (m, 3H).

1,2,3-thiadiazole-carbonitriles were prepared as illustrated in Example 17. The reaction of an appropriate benzoylacetonitrile with methyl hydrazinocarboxylate yields the desired thidiazolecarbonitriles in one pot (*Synthesis*, 1985, (11), 1048).

EXAMPLE 17

5-Cyano-4-(2-chlorphenyl)-1,2,3-thiadiazole

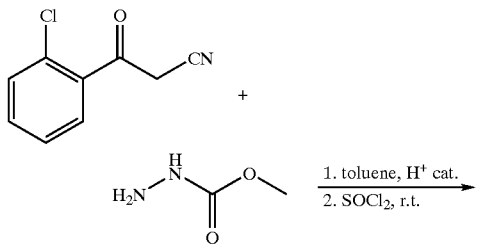

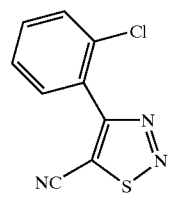

A mixture of 2-chlorobenzoylacetonitrile (3.58 g, 20 mmol), methyl hydrazinocarboxylate (1.80 g, 20 mmol) along with a catalytic amount of p-toluenesulfonic acid in 75 mL of toluene was heated to reflux in a flask equipped with a Dean-Stark trap. After refluxing overnight 3.8 mL of $H_2O$ had been collected. The solution was allowed to cool to room temperature and concentrated in vacuo. The residue was taken up in ethyl acetate and washed with $H_2O$ (2×150 mL) and dried over anhydrous MgSO$_4$. The mixture was filtered and concentrated in vacuo to give 4.71 g of a reddish gum.

A portion of the intermediate (1.9 g, 8 mmol) was transferred to a 100 mL round bottom flask and treated with thionyl chloride (20 mL). After stirring at room temperature for 3 hours, TLC analysis showed one major product. The thionyl chloride was removed in vacuo. The residue was taken up in ethyl acetate (150 mL), washed with $H_2O$ (2×150 mL), dried over anhydrous MgSO$_4$, filtered and concentrated in vacuo. The residue was chromatographed on silica gel (MPLC), eluting with a serial dilution of hexane to 5% ethyl acetate. Isolation of the major product gave 600 mg (34% yield) of the desired product as a colorless oil: $^1H$ NMR (CDCl$_3$) δ7.68–7.62 (m, 2H), 7.59–7.52 (m, 1H), 7.52–7.46 (m, 1H).

EXAMPLE 18

3-(2-chloro-6-fluorophenyl)-5-(3-phenyl-4-chloroisothiazo-5-yl)-1-methyl[1,2,4]triazole A mixture of 4-chloro-3-phenylisothiazole -5-carbonitrile (0.98 g, 4.4 mmol), N-methylbenzenesulfonyl)-N-methyl-(2-chloro-6-fluorobenz)hydrazonoyl chloride of Example 15C (1.73 g, 4.8 mmol) and aluminum chloride (0.70 g, 5.3 mmol) in 1,2-dichlorobenzene was placed in an oil bath preheated to 130° C. After stirring at 130–140° C. for 30 min, the reaction mixture was allowed to cool, poured into 1N NaOH (50 mL) and extracted with ethyl acetate (3×50 mL). The combined organic phases were washed with $H_2O$ (1×50 mL), saturated NaCl (1×50 mL), dried over anhydrous MgSO$_4$, filtered and concentrated to give 2.44 g of a brown oil. This was chromatographed on silica gel (MPLC), eluting with 80% hexane/20% ethyl acetate. Isolation of the major product gave 1.187 g (66% yield) of the desired product as a tan glass. This slowly solidified into a tan solid: mp 94–97° C.; $^1H$ NMR (CDCl$_3$) δ7.93–7.90 (m, 2H), 7.53–7.50 (m, 3H), 7.40–7.31 (m, 2H), 7.16–7.10 (m, 1H), 4.10 (s, 3H)

EXAMPLE 19

3-(2-chloro-6-fluorophenyl)-5-(4-bromo-1-ethyl-3-methylpyrazo-5-yl)-1-methyl[1,2,4]triazole Aluminum chloride (0.93 g, 7.0 mmol) was added to a solution of 4-bromo-1-ethyl-3-methylpyrazole-5-carbonitrile (1.24 g, 5.8 mmol) and N-methylbenzenesulfonyl)-N-methyl-(2-chloro-6- fluorobenz)hydrazonoyl chloride of Example 15C (2.31 g, 6.4 mmol) in 10 mL of 1,2-dichlorobenzene. The resultant mixture was placed in an oil bath preheated to 130° C. After stirring at 130–140° C. for 30 min, the reaction mixture was allowed to cool, diluted with CH$_2$Cl$_2$ (100 mL) and washed with 1N NaOH (1×50 mL), H$_2$O (1×50 mL) and saturated NaCl (1×50 mL). The organic phases was dried over anhydrous MgSO$_4$, filtered and concentrated to give 3.17 g of a yellow oil. Crystallization from hexane/ethyl acetate and vacuum oven drying (70–80° C.) gave 1.301 g (56% yield) of the desired product as a tan solid: mp 110–112° C.; $^1$H NMR (CDCl$_3$) δ7.42–7.31 (m, 2H), 7.16–7.11 (m, 1H), 4.21 (q, 2H), 4.01 (s, 3H), 2.33 (s, 3H), 1.36 (t, 3H).

EXAMPLE 20

3-(2-chloro-6-fluorophenyl)-5-(4-methyl-1,2,3-thiadiazo-5-yl)-1-methyl[1,2,4]triazole A mixture of aluminum chloride (0.53 g, 4 mmol) in 1,2-dichlorobenzene (10 mL) was heated to 140° C. in an oil bath and then treated with 5-cyano-4-methyl-1,2,3-thiadiazole (0.50 g, 4 mmol) followed by the chloroimine of Example 15C (1.44 g, 4 mmol). Once all of the chloroimine had been consumed the reaction was allowed to cool to 70° C. and then treated with chilled 2N NaOH (50 mL) and extracted with CH$_2$Cl$_2$ (1×100 mL). The CH$_2$Cl$_2$ layer was washed with H$_2$O (2 100 mL) and dried over anhydrous MgSO$_4$. The solution was filtered and concentrated in vacuo to give a brown gum. This was chromatographed on silica gel (MPLC), eluting with a serial dilution of hexane to 15% ethyl acetate. Isolation of the major product gave 0.49 g (40% yield) of the desired product as a yellow oil: $^1$H NMR (CDCl$_3$) δ7.4–7.3 (m, 2H), 7.15–7.05 (m, 1H), 4.05 (s, 3H), 2.95 (s, 3H).

EXAMPLE 21

3-(2-chloro-6-fluorophenyl)-5-(4-methyl-2-chlorothiazo-5-yl)-1-methyl[1,2,4]triazole A mixture of 2-chloro-4-methyl-5-thiazolecarbonitrile (0.33 g, 2.1 mmol), the chloroimine of Example 15C (0.83 g, 2.2 mmol) and aluminum chloride (0.28 g, 2.1 mmol) in 15 mL of 1,2-dilchlorobenzene was placed in an oil bath that was preheated to 135° C. After ~40 minutes the reaction was allowed too cool to room temperature and the solvent removed in vacuo. The resultant dark residue was taken up in ethyl acetate (150 mL) and washed with H$_2$O (2×125 mL). The organic layer was dried over anhydrous MgSO$_4$, filtered, treated with 50 mL of silica gel and concentrated in vacuo. The material was chromatographed over silica gel (MPLC), eluting with a serial dilution of hexanes to 10% ethyl acetate. Isolation of the major product gave 0.31 g (43% yield) of the desired product as a gold oil: $^1$H NMR (CDCl$_3$) δ7.4–7.3 (m, 2H), 7.2–7.1 (m, 1H), 4.0 (s, 3H), 2.5 (s, 3H).

EXAMPLE 22

3-(2-chloro-6-fluorophenyl)-5-(1,5-dimethylpyrrol-2-yl)-1-methyl[1,2,4]triazole

A mixture of 1,5-dimethyl-2-pyrrolecarbonitrile (0.51 g, 4.24 mmol), the chloroimine of Example 15C (1.44 g, 4.0 mmol) and aluminum chloride (373 mg, 2.8 mmol) in 1,2-dichlorobenzene (2 mL) was heated to 130° C. After 45 minutes the mixture was diluted with CH$_2$Cl$_2$ and washed with 2N NaOH, saturated NaCl, dried over anhydrous MgSO$_4$, filtered and concentrated. The crude material was chromatographed over silica gel (MPLC), eluting with CH$_2$Cl$_2$. This gave 155 mg (13% yield) of the desired product as clear oil.

Compounds of the invention can also be prepared by the process illustrated in the following scheme:

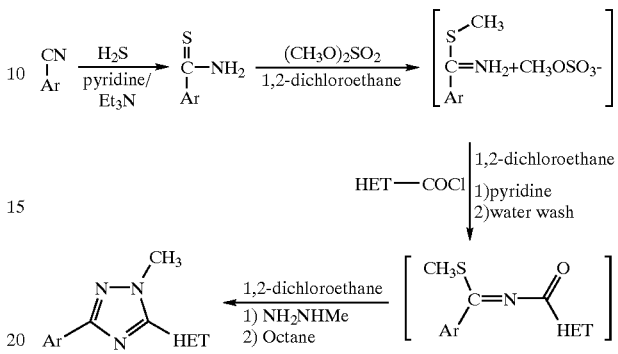

The first step in the foregoing scheme is preparation of the thioamide starting material. Any of the methods known in the chemical literature can be used for this thioamide formation reaction. Sodium sulfide can be used as the sulfur source, but it has been found most convenient to use hydrogen sulfide gas. Reaction temperatures used are in the −35° to 50° C. range, with −10° to RT most convenient. Any common solvent compatible with the reaction conditions can be used. Pyridine and ethanol are suitable. Any common amine base, for example triethylamine, can be used.

The next three distinct chemical transformations are most conveniently carried out in one process step, without isolation of two intermediates. The two intermediates can be isolated and characterized if desired. The first transformation converts the thioamide to the thioimidate. Any known imidate forming procedure known in the literature can be used for this transformation. Common methylating agents such as methyliodide, methylbromide and dimethyl sulfate can be used. Any common solvent compatible with the reaction conditions can be used, with toluene, acetonitrile, THF, and 1,2-dichloroethane most convenient. Reaction temperatures range from RT to the reflux temperature of the solvent. The thioimidate can be isolated as its salt or used directly without isolation in the next transformation.

The thioimidate is next acylated with the appropriate heterocyclic carbonyl chloride to give the acylated adduct. This adduct can be isolated and characterized if desired, but was found to be most conveniently used directly without isolation. Any known acylation conditions can be used for this transformation. Any common organic and inorganic base can be used, with Na$_2$C$_3$, NaHCO$_3$, pyridine and triethylamine most convenient. Solvents preferred include THF, dichloromethane, and 1,2-dichloroethane, but any solvent compatible with the reaction conditions can be used. Reaction temperatures in the 0° to 60° C. range are suitable, with temperatures near RT most convenient.

The acylated adduct is finally cyclized to the 1,2,4-triazole ring system by treatment with methylhydrazine. A two step procedure using hydrazine to give the unsubstituted triazole followed by methylation could be used, but it is convenient to use methylhydrazine directly. The methylhydrazine can be added neat or as a solution in a compatible solvent such as water. Any solvent compatible with the reaction conditions can be used, with toluene, THF, and 1,2-dichloroethane preferred. The methylhydrazine can be added all at once to the reaction mixture, or added in portions over a 1 hour time period. The cyclization can be carried out in the temperature range of RT to reflux temperature of the solvent being used. It is most convenient to use 1,2-dichloroethane at a cyclization temperature of 70° C.

The acylated adducts of formula

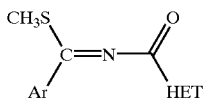

are novel compounds and are one aspect of the present invention.

EXAMPLE 23

N-(5-Methyl-3-phenylisoxazol-5-oyl)-S-methylthio-2-chloro-6-fluorobenzimidate

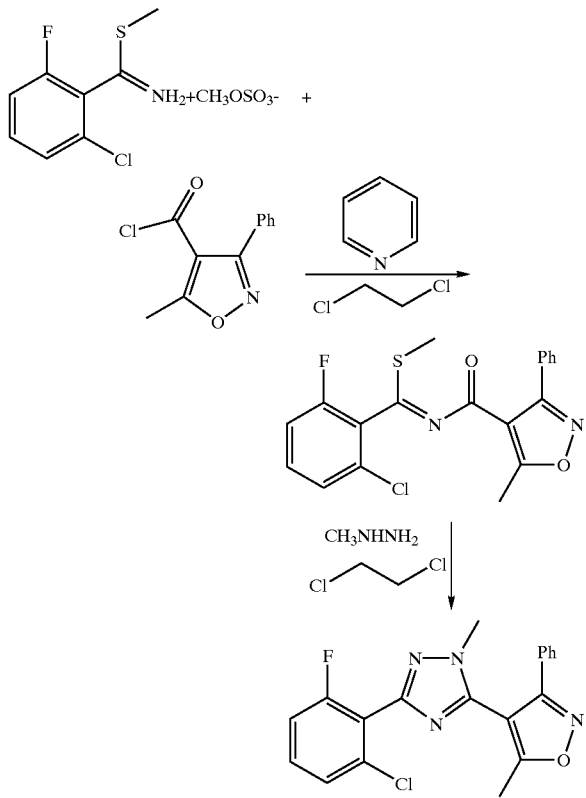

Pyridine (0.85 mL, 10.5 mmol) was added dropwise to a mixture of 5-methyl-3-phenylisoxazole-4-carbonyl chloride (1.11 g, 5.0 mmol) and the thioimidate salt (1.58 g, 5.0 mmol) in 10 mL of 1,2-dichloroethane, under $N_2$, at room temperature. After four hours at room temperature the reaction mixture was poured into $H_2O$ (50 mL) and extracted with ethyl acetate (3×50 mL). The combined organic extracts were washed with $H_2O$ (1×50 mL), saturated sodium chloride (1×50 mL), dried over anhydrous $MgSO_4$, filtered and concentrated to give 1.77 g of a white paste. This was chromatographed on silica gel (MPLC), eluting with $CH_2Cl_2$. Isolation of the major product gave 0.584 g (30% yield) of the desired product as a white solid: mp 121–123° C.; $_1$H NMR (CDCl$_3$) δ7.49–7.27 (m, 6H), 7.17 (d, 1H), 7.02–6.97 (m, 1H), 2.59 (s, 3H), 2.10 (s, 3H).

3-(2-Chloro-6-fluorophenyl)-5-(5-methyl-3-phenylisoxazol-4-yl)-1-methyl[1,2,4]triazole Methylhydrazine (100 mL, 2.0 mmol) was added dropwise to a solution of the thioimidate (0.508 g, 1.3 mmol) in 2 mL of 1.2-dichloroethane while heating to reflux. After refluxing for two hours the reaction was allowed to cool to room temperature while stirring overnight. The reaction mixture was concentrated in vacuo and the residue chromatographed on silica gel (MPLC), eluting with 75% hexane/25% ethyl acetate. Isolation of the major product gave 0.406 g (85% yield) of the desired product as a white solid: mp 120–125° C.; $^1$H NMR(CDCl$_3$) δ7.50–7.31 (m, 7H), 7.16–7.10 (m, 1H), 3.46 (s, 3H), 2.58 (s, 3H).

Phytologically acceptable acid addition salts of the compounds of the formula (1) are also within the scope of the invention. For example, boron tetrafluoride, hydrogen chloride, hydrogen bromide, hydrogen iodide, hydrogen sulfate or organic salts may be used.

The compounds identified in Table 1 were prepared and tested.

TABLE 1

Compounds prepared and tested

[Structure: 2,6-disubstituted phenyl (R7, R8) attached to 1-methyl-1,2,4-triazole bearing HET group]

| cmpd number | R⁷ | R⁸ | HET | mp | CA[a] | TSSM[b] | WF[c] |
|---|---|---|---|---|---|---|---|
| 1 | F | F | 4-Cl-3-methyl-5-methyl-isothiazole | 73–75 | A | A | G |
| 2 | F | F | 4-methyl-5-methyl-isothiazole | 88–90 | D | B | |
| 3 | F | Cl | 4-methyl-5-methyl-isothiazole | 143–144 | B | A | G |
| 4 | F | F | 4-Br-3-CN-5-methyl-isothiazole | 168–170 | A | G | G |
| 5 | F | F | 4-Cl-3-phenyl-5-methyl-isothiazole | 122–123 | B | A | G |
| 6 | F | Cl | 4-Cl-3-phenyl-5-methyl-isothiazole | 94–97 | A | A | G |
| 7 | F | F | 4-Br-3-phenyl-5-methyl-isothiazole | 161–162 | B | G | E |

TABLE 1-continued

Compounds prepared and tested

| cmpd number | R[7] | R[8] | HET | mp | CA[a] | TSSM[b] | WF[c] |
|---|---|---|---|---|---|---|---|
| 8 | F | Cl | 4-bromo-5-methyl-3-phenyl-isothiazole | 118–119 | B | C | G |
| 9 | F | F | 3-(4-chlorophenyl)-5-methyl-isoxazole | 188–190 | E | F | G |
| 10 | F | Cl | 3-(4-chlorophenyl)-5-methyl-isoxazole | 165–167 | F | B | |
| 11 | F | F | 4-bromo-3-(4-chlorophenyl)-5-methyl-isothiazole | 183–185 | A | A | G |
| 12 | F | Cl | 4-bromo-3-(4-chlorophenyl)-5-methyl-isothiazole | 92–96 | A | A | G |

TABLE 1-continued
Compounds prepared and tested
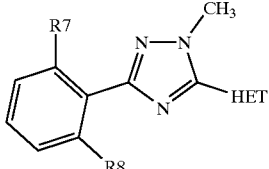
| cmpd number | R⁷ | R⁸ | HET | mp | CA[a] | TSSM[b] | WF[c] |
|---|---|---|---|---|---|---|---|
| 13 | F | F | 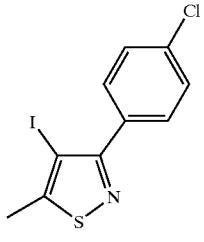 | 186–187 | F | G | |
| 14 | F | F | 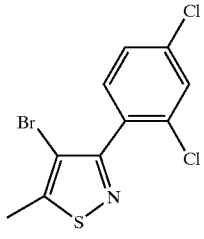 | 172–173 | B | G | G |
| 15 | F | F | 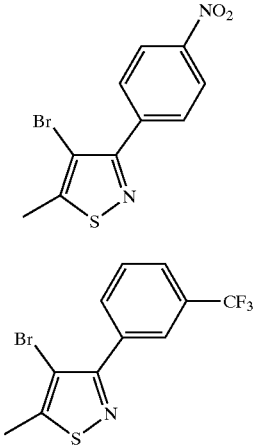 | 193–195 | F | G | G |
| 16 | F | F | 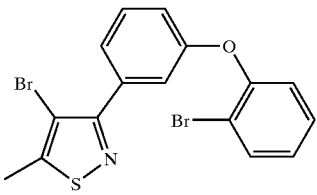 | 115–117 | B | G | F |
| 17 | F | F | 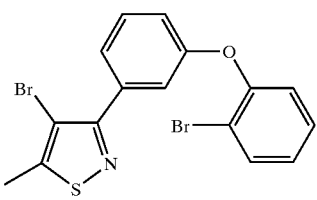 | glass | B | F | |
| 18 | F | Cl |  | oil | C | F | |

TABLE 1-continued

Compounds prepared and tested

| cmpd number | R⁷ | R⁸ | HET | mp | CA[a] | TSSM[b] | WF[c] |
|---|---|---|---|---|---|---|---|
| 19 | F | F | 4-Br-5-methyl-3-(pyridin-2-yl)isothiazole | 116–118 | C | A | |
| 20 | F | Cl | 4-Br-5-methyl-3-(pyridin-2-yl)isothiazole | glass | B | A | |
| 21 | F | Cl | 4-Cl-5-methyl-3-(pyridin-2-yl)isothiazole | glass | B | A | |
| 22 | F | Cl | 5-methyl-3-(pyridin-2-yl)isothiazole | 166–167 | F | A | |
| 23 | F | F | 4,5-dichloro-3-methylisothiazole | 86–87 | F | E | |
| 24 | F | F | 3-(2,6-dichlorophenyl)-4-methylisothiazole | 145–147 | F | E | |

TABLE 1-continued

Compounds prepared and tested

| cmpd number | R⁷ | R⁸ | HET | mp | CAᵃ | TSSMᵇ | WFᶜ |
|---|---|---|---|---|---|---|---|
| 25 | F | F | 4-methyl-3-(3-chlorophenyl)isothiazole | oil | F | G | |
| 26 | F | F | 4-methyl-3-(methylthio)-5-methylisothiazole | 122–123 | C | F | G |
| 27 | F | F | 5-methylisoxazole | 110–112 | F | F | |
| 28 | F | F | 3,5-dimethylisoxazole | 96–99 | F | G | B |
| 29 | F | F | 4-chloro-3,5-dimethylisoxazole | 94–97 | B | G | |
| 30 | F | F | 3-t-Bu-5-methylisoxazole | oil | D | G | F |
| 31 | F | F | 3,4,5-trimethylisoxazole | 118–120 | A | F | F |
| 32 | F | F | 4-methyl-3-phenyl-5-methylisoxazole | 115–117 | A | F | |

TABLE 1-continued

Compounds prepared and tested

| cmpd number | R⁷ | R⁸ | HET | mp | CA[a] | TSSM[b] | WF[c] |
|---|---|---|---|---|---|---|---|
| 33 | F | F | 3-(2-chlorophenyl)-4-methyl-5-methylisoxazole | 160–162 | F | G | |
| 34 | F | F | 3-(2,6-dichlorophenyl)-4-methyl-5-methylisoxazole | 212–214 | F | G | |
| 35 | F | F | 3-methyl-5-methylisoxazole | 83–85 | B | G | |
| 36 | F | F | 3-methyl-5-t-butylisoxazole | 83–85 | G | B | |
| 37 | F | F | 4,5-dimethylthiazole | oil | B | A | G |
| 38 | F | F | 4-chloro-5-methylthiazole | 129–133 | A | A | G |
| 39 | F | F | 4-methyl-2-chloro-5-methylthiazole | gum | A | A | G |
| 40 | F | Cl | 4-methyl-2-chloro-5-methylthiazole | oil | A | A | F |

TABLE 1-continued
Compounds prepared and tested
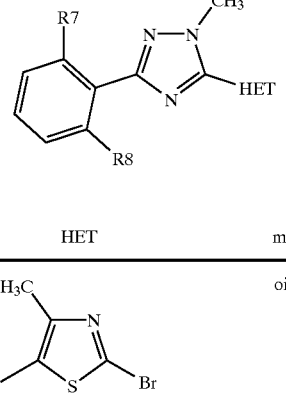
| cmpd number | R⁷ | R⁸ | HET | mp | CA[a] | TSSM[b] | WF[c] |
|---|---|---|---|---|---|---|---|
| 41 | F | F | 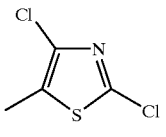 | oil | A | A | G |
| 42 | F | F | 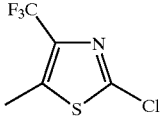 | 89–91 | B | A | G |
| 43 | F | F | 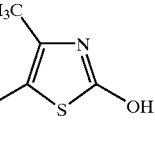 | 94–98 | F | G | |
| 44 | F | F | 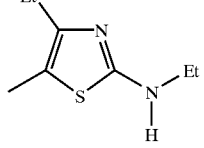 | 219–224 | F | E | |
| 45 | F | F | 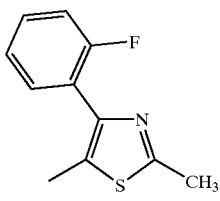 | oil | C | G | |
| 46 | F | F | 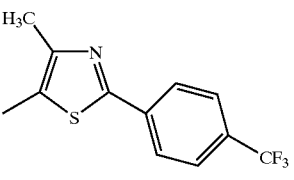 | 138–141 | F | G | G |
| 47 | F | F | 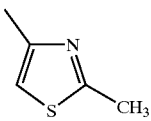 | 128–131 | D | A | G |
| 48 | F | F |  | 127–130 | D | G | G |

TABLE 1-continued
Compounds prepared and tested
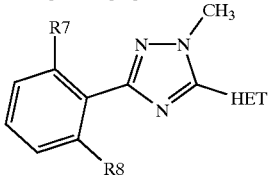
| cmpd number | R[7] | R[8] | HET | mp | CA[a] | TSSM[b] | WF[c] |
|---|---|---|---|---|---|---|---|
| 49 | F | Cl | 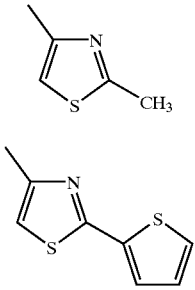 | 137–139 | F | C | G |
| 50 | F | F | 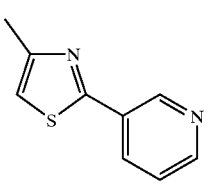 | 176–180 | A | G | G |
| 51 | F | F | 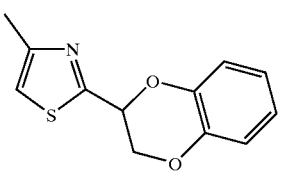 | 179–186 | F | G | |
| 52 | F | F | 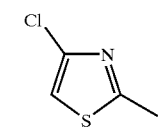 | 144–145 | G | G | |
| 53 | F | F | 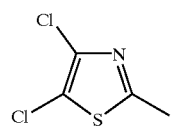 | 147–148 | A | | |
| 54 | F | F | 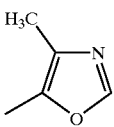 | 100–102 | F | G | |
| 55 | F | F | 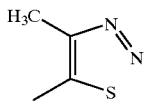 | 113–115 | F | F | |
| 56 | F | F | 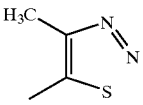 | 80–83 | B | G | F |
| 57 | F | Cl | 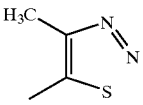 | oil | B | A | G |

TABLE 1-continued
Compounds prepared and tested
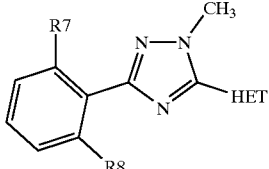
| cmpd number | R⁷ | R⁸ | HET | mp | CAᵃ | TSSMᵇ | WFᶜ |
|---|---|---|---|---|---|---|---|
| 58 | F | F | 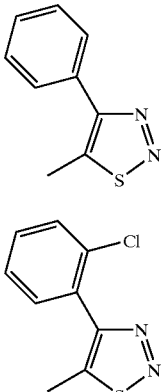 | oil | A | C | G |
| 59 | F | Cl | 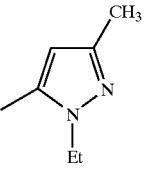 | 150–152 | F | D | |
| 60 | F | F | 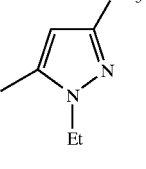 | 69–70 | B | G | F |
| 61 | F | Cl | 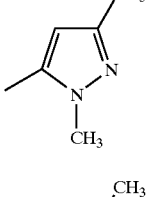 | paste | F | G | |
| 62 | F | F | 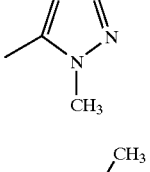 | 87–88 | A | G | E |
| 63 | F | Cl | 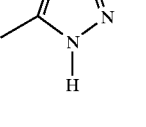 | 90–92 | A | G | F |
| 64 | F | F |  | 188–190 | A | G | |

TABLE 1-continued
Compounds prepared and tested
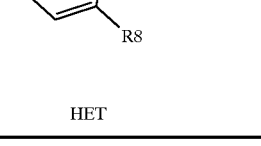
| cmpd number | R⁷ | R⁸ | HET | mp | CA[a] | TSSM[b] | WF[c] |
|---|---|---|---|---|---|---|---|
| 65 | F | F | 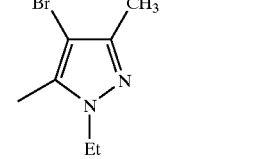 | 77–79 | B | G | |
| 66 | F | Cl | 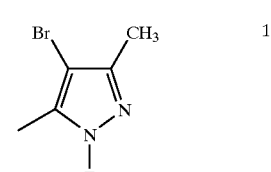 | 110–112 | F | A | |
| 67 | F | F | 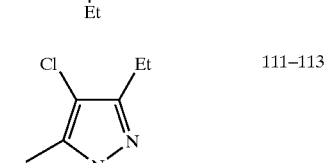 | 111–113 | A | F | |
| 68 | F | F | 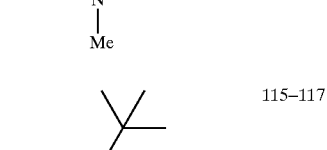 | 115–117 | C | G | |
| 69 | F | F | 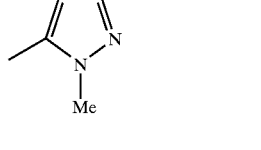 | 177 | F | G | |
| 70 | F | F |  | oil | B | G | E |

TABLE 1-continued

Compounds prepared and tested

| cmpd number | R[7] | R[8] | HET | mp | CA[a] | TSSM[b] | WF[c] |
|---|---|---|---|---|---|---|---|
| 71 | F | F | 3,5-dimethyl-1-methyl-pyrazole | 135–137 | A | G | G |
| 72 | F | Cl | 3,5-dimethyl-1-methyl-pyrazole | 126–128 | A | C | G |
| 73 | F | F | 3,5-dimethyl-1-ethyl-pyrazole | 83–85 | A | G | |
| 74 | F | Cl | 3,5-dimethyl-1-ethyl-pyrazole | 86–88 | A | F | F |
| 75 | F | Cl | 4-chloro-3-methyl-1-methyl-pyrazole | 174–176 | F | G | B |
| 76 | F | Cl | 5-chloro-3,4-dimethyl-1-methyl-pyrazole | 88–89 | B | A | F |
| 77 | F | Cl | 5-chloro-4-methyl-3-CF$_3$-1-methyl-pyrazole | glass | F | A | F |

TABLE 1-continued

Compounds prepared and tested

| cmpd number | R⁷ | R⁸ | HET | mp | CA[a] | TSSM[b] | WF[c] |
|---|---|---|---|---|---|---|---|
| 78 | F | F | 4-methyl-5-nitro-1-methyl-pyrazole (O₂N, Me) | 177–178 | A | A | G |
| 79 | F | F | 4-methyl-5-CF₃-1-(4-chlorophenyl)-pyrazole | 123–125 | A | G | G |
| 80 | F | F | 4-methyl-5-n-Pr-1-(4-chlorophenyl)-pyrazole | 158–160 | F | G | F |
| 81 | F | Cl | 4-methyl-5-pyrrolyl-1-(3-chlorophenyl)-pyrazole | 177–178 | F | G | |
| 82 | F | Cl | 4-methyl-3-SCH₃-1-phenyl-pyrazole | 166–167 | F | G | |

TABLE 1-continued
Compounds prepared and tested
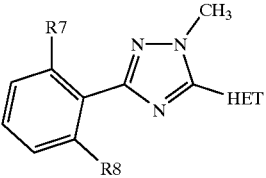
| cmpd number | R⁷ | R⁸ | HET | mp | CA[a] | TSSM[b] | WF[c] |
|---|---|---|---|---|---|---|---|
| 83 | F | Cl | 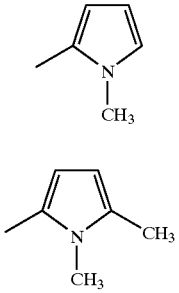 | oil | B | D | |
| 84 | F | Cl | 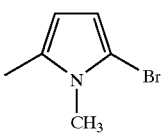 | oil | A | C | |
| 85 | F | F | 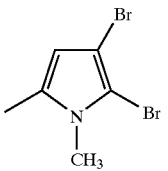 | 95–100 | B | E | G |
| 86 | F | F | 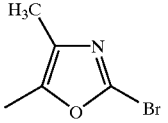 | 125–127 | A | G | G |
| 87 | F | F | 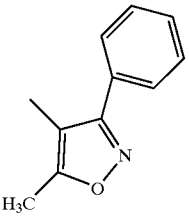 | 125–129 | G | D | |
| 88 | F | Cl | 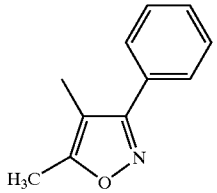 | 120–125 | | | |
| 89 | F | Cl | | 120–125 | F | | F |

TABLE 1-continued

Compounds prepared and tested

[Structure: phenyl ring with R7 and R8 substituents, connected to a 1-methyl-1,2,4-triazole bearing HET group]

| cmpd number | R⁷ | R⁸ | HET | mp | CA<sup>a</sup> | TSSM<sup>b</sup> | WF<sup>c</sup> |
|---|---|---|---|---|---|---|---|
| 90 | F | F | 4-methyl-5-methyl-2-(4-chlorophenyl)thiazole | 164–166 | F | A | F |
| 91 | F | F | 4-methyl-5-methyl-2-CF₃-thiazole | paste | C | F | F |
| 92 | F | F | 4-methyl-5-methyl-2-Br-oxazole | 125–129 | F | F | F |
| 93 | F | F | 4-methyl-5-CF₃-2-(4-CF₃-phenyl)oxazole | 184–185 | F | F | F |

<sup>a</sup>CA refers to to activity at 50 ppm against cotton aphids (*aphis gossypii*)
<sup>b</sup>TSSM refers to activity at 100 ppm against twospotted spider mite (*tetranychus uriticae*)
<sup>c</sup>WF refers to activity at 800 ppm against sweetpotato whitefly (*bemisia tabaci*)

In each case the rating scale is as follows

| % Mortality* | Rating |
|---|---|
| 91–100 | A |
| 81–90 | B |
| 71–80 | C |
| 61–70 | D |
| 51–60 | E |
| <51 | E |
| Inactive | G |

Insecticide and Miticide Utility

The compounds of the invention are useful for the control of insects, mites, and aphids. Therefore, the present invention also is directed to a method for inhibiting an insect, mite, or aphid which comprises applying to a locus of the insect or mite an insect- or mite-inhibiting amount of a compound of formula (1).

The compounds are useful for reducing populations of insects and mites and are useful in a method of inhibiting an insect or mite population which comprises applying to a locus of the insect or mite an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts that the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used. The terms "insect-inactivating amount" and "mite-inactivating amount" are used to describe the amount, which is sufficient to cause a measurable reduction in the treated insect or mite, population. Generally an amount in the range from about 1 to about 1000 ppm active compound is used.

In a preferred embodiment, the present invention is directed to a method for inhibiting a mite or aphid which comprises applying to a plant an effective mite- or aphid-inactivating amount of a compound of formula (1.

Insecticidal Test for Cotton Aphid (*Aphis gossypii*)

To prepare spray solutions, 2 mg of each test compound was dissolved into 2 mL of a 90:10 acetone:ethanol solvent. This 2 mL of chemical solution was added to 38 mL of water containing 0.05% Tween 20 surfactant to produce a 50 ppm spray solution.

Squash cotyledons were infested with cotton aphid (all life stages16–20 hours prior to application of spray solution. The solution was sprayed on both sides of each infested squash cotyledon (0.5 mL×2 each side with a sweeping action using a total of 2 mL of spray solution. The plants were allowed to air dry and held for 3 days in a controlled room at 26° C. and 40% RH after which time the test was graded. Grading was by actual count using a dissecting microscope and comparison of test counts to the untreated check. Results are given in Table 1 as percent control based on population reduction versus the untreated.

Insecticidal Test for Two-spotted Spider Mite (*Tetranychus urticae*)

Ovicide Method

Ten adult female two-spotted spider mites were placed on eight 2.2 cm leaf discs of cotton leaf, allowed to oviposit over 24 hours, and thereafter removed. The leaf discs were immersed in 100 ppm test solutions for 3 seconds, then allowed to dry with sixteen discs left untreated as a negative control. Discs were placed on an agar substrate and held at 24° C. and 90% relative humidity for 6 days. Percent control based on the number of hatched larvae on treated discs and the number on untreated discs is reported in Table 1.

Evaluation of Tests Compounds on Sweetpotato Whitefly (*Bemisia tabacia*) Under Laboratory Conditions Four mg of each test compound was dissolved by adding 5 ml of a 90:10 acetone:ethanol solvent mixture to the vial containing the sample compound. This solution was added to 15 ml of water containing 0.05% Tween 20 surfactant to produce 20 ml of an 200 ppm spray solution.

Five-week-old cotton plants reared in a greenhouse were stripped of all foliage except for the two uppermost true leaves that were greater than 5 cm in diameter. These plants were then placed into a laboratory colony of whiteflies for three days for oviposition by the colony females. All whiteflies were then removed from the test plants with pressurized air. The spray solution was then applied to the test plants with a hand-held syringe fitted with hollow cone nozzle. One mL spray solution was applied to each leaf top and bottom for a total of 4 mL per plant. Four replications of each test compound utilized a total of 16 mL spray solution. Plants were air dried and then placed in a holding chamber (26° C. and 40% RH for 21 days. Compound efficacy was evaluated by counting, under a dissecting microscope, the number of spent pupal cases per leaf. A spent pupal case represents a whitefly egg that has undergone full development to achieve adult status, thus indicating lack of control.

Percent control based on reduction of spent pupal cases of a test compound compared to solution-only (no test compound sprayed plants is reported in Table 1.

In addition to being effective against mites, aphids, and insects when applied to foliage, compounds of formula (1) have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of formula (1).

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 5–20 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the practice of the present invention.

A. 0.75 Emulsifiable Concentrate

| | |
|---|---|
| Compound of formula (1) | 9.38% |
| "TOXIMUL D" (nonionic/anionic surfactant blend | 2.50% |
| "TOXIMUL H" (nonionic/anionic surfactant blend | 2.50% |
| "EXXON 200" (naphthalenic solvent | 85.62% |

B. 1.5 Emulsifiable Concentrate

| | |
|---|---|
| Compound of formula (1) | 18.50% |
| "TOXIMUL D" | 2.50% |
| "TOXIMUL H" | 2.50% |
| "EXXON 200" | 76.50% |

C. 1.0 Emulsifiable Concentrate

| | |
|---|---|
| Compound of formula (1) | 12.5% |
| N-methylpyrrolidone | 25.00% |
| "TOXIMUL D" | 2.50% |
| "TOXIMUL H" | 2.50% |
| "EXXON 200" | 57.50% |

D. 1.0 Aqueous Suspension

| | |
|---|---|
| Compound of formula (1) | 12.00% |
| "PLURONIC P-103"(block copolymer of propylene oxide and ethylene oxide, surfactant | 1.50% |
| "PROXEL GXL"(bio~ide/preservative | .05% |
| "AF-100"(silicon based antifoam agent | .20% |
| "REAX 88B"(lignosulfonate dispersing agent | 1.00% |
| propylene glycol | 10.00% |
| veegum | .75% |
| xanthan | .25% |
| water | 74.25% |

E. 1.0 Aqueous Suspension

| | |
|---|---|
| Compound of formula (1) | 12.50% |
| "MAKON 10" (10 moles ethyleneoxide nonylphenol surfactant | 1.00% |
| "ZEOSYL 200" (silica | 1.00% |
| "AF-100" | 0.20% |
| "AGRIWET FR" (surfactant | 3.00% |
| 2% xanthan hydrate | 10.00% |
| water | 72.30% |

F. 1.0 Aqueous Suspension

| | |
|---|---|
| Compound of formula (1) | 12.50% |
| "MAKON 10" | 1.50% |
| "ZEOSYL 200" (silica | 1.00% |
| "AF-100" | 0.20% |
| "POLYFON H" (lignosulfonate dispersing agent | 0.20% |
| 2% xanthan hydrate | 10.00% |
| water | 74.60% |

G. Wettable Powder

| | |
|---|---|
| Compound of formula (1) | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |

H. 1.0 Aqueous Suspension

| | |
|---|---|
| Compound of formula (1) | 12.40% |
| "TERGITOL 158-7" | 5.00% |
| "ZEOSYL 200" | 1.0% |
| "AF-lG0" | 0.20% |
| "POLYFON H" | 0.50% |
| 2% xanthan solution | 10.00% |
| tap water | 70.90% |

I. 1.0 Emulsifiable Concentrate

| | |
|---|---|
| Compound of formula (1) | 12.40% |
| "TOXIMUL D" | 2.50% |
| "TOXIMUL H" | 2.50% |
| "EXXON 200" | 82.60% |

J. Wettable Powder

| | |
|---|---|
| Compound of formula (1) | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |

K. 0.5 Emulsifiable Concentrate

| | |
|---|---|
| Compound of formula (1) | 6.19% |
| "TOXIMUL H" | 3.60% |

| | |
|---|---|
| "TOXIMUL D" | 0.40% |
| "EXXON 200" | 89.81% |

L. Emulsifiable Concentrate

| | |
|---|---|
| Compound of formula (1) | 5 to 48 |
| surfactant or surfactant blend | 2 to 20% |
| Aromatic Solvent or Mixture | 55 to 75% |

We claim:

1. A compound of the formula (1)

$$Ar\!-\!\underset{N}{\overset{N-N}{\diagdown}}\!-\!HET \quad (1)$$
                R¹ wherein

Ar is phenyl substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, pheneyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

$R^1$ is $(C_1-C_6)$ alkyl; $(C_1-C_6)$ haloalkyl; $C_2-C_6$ alkenyl; $(C_2-C_6)$ alkynyl; or $(C_1-C_6)$ alkoxy-substituted $(C_1-C_6)$ alkyl;

HET is a group selected from

[structures with R2, R3, R4 substituents on thiazole, oxazole, isoxazole, thiazole, pyrazole, pyrrole, and thiadiazole rings]

and $R^2$ is selected from H; halo; $(C_1-C_6)$ alkyl; $(C_7-C_{21})$ straight chain alkyl; hydroxy; $(C_1-C_6)$ alkoxy; $(C_1-C_6)$ haloalkyl; $(C_1-C_6)$ haloalkoxy; $(C_1-C_6)$ alkoxy-substituted $(C_1-C_6)$ alkyl; $(C_1-C_6)$ alkoxy-substituted $(C_1-C_6)$ alkoxy; $(C_2-C_6)$ alkenyl; $(C_2-C_6)$ haloalkenyl; CN; $NO_2$; $CO_2R^6$; $CON(R^6)_2$; $(C_3-C_6)$ cycloalkyl; $S(O)_m R^6$; SCN; naphthyl; naphthyl substituted with one or more groups independently selected from halo, halo $(C_1-C_4)$ alkyl, CN, $NO_2$, $(C_1-C_4)$ alkyl, $(C_3-C_4)$ branched alkyl, phenyl, $(C_1-C_4)$ alkoxy, or halo $(C_1-C_4)$ alkoxy; phenyl; phenyl substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy; $-(CH_2)_n R^6$; $-CH{=}CHR^6$; $-C{=}CR^6$; $-CH_2 OR^6$; $-CH_2 SR^6$; $-CH_2 NR^6 R^6$; $-OCH_2 R^6$; $-SCH_2 R^6$;

$NR^6 CH_2 R^6$; $-NR^6 C(O) R^6$; $-NR^6 C(O) OR^6$;

$-NR^6 C(O) N(R^6)_2$; $R^6 C({=}N{-}OR^6)$; $-C(O)H$;

$-OC(O)R^6$; or $-SC(O)R^6$;

$R^3$ is H; halo; $(C_1-C_6)$ alkyl; $(C_1-C_6)$ alkoxy; $(C_1-C_6)$ haloalkyl; $(C_1-C_6)$ haloalkoxy; CN; $CO_2 R^6$; $CON(R^6)_2$; or $S(O)_m$ alkyl; or $R^2$ and $R^3$ combine to form a 5 or 6 member saturated or unsaturated carbocyclic ring which may be substituted by 1 or 2 halo; $(C_1-C_6)$ alkyl; $(C_1-C_6)$ alkoxy; or $C_1-C_6$ haloalkyl groups;

$R^4$ is H; $(C_1-C_6)$ alkyl; $(C_1-C_6)$ haloalkyl; $(C_2-C_6)$ alkenyl; $(C_2-C_6)$ alkynyl; phenyl; or phenyl substituted with one or more groups independently selected from halo, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxl, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

$R^6$ is H; $(C_1-C_6)$ alkyl; $(C_1-C_6)$ haloalkyl; $(C_2-C_6)$ alkenyl; $(C_2-C_6)$ alkynyl; phenyl; or phenyl substituted with one or more groups indpendently selected from halo, $(C_1-C_{10})$ alkyl, branched $(C_{3-6})$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyl, benzoyl, $(C_1-C_4)$ alkanoyloxy, $(C_1-C_4)$ alkoxycarbonyl, phenoxycarbonyl, or benzoyloxy;

m is 0, 1 or 2; and n is 1 or 2;

or a phytologically acceptable acid addition salt thereof.

2. A compound of claim 1 wherein Ar is a group of the formula

[benzene ring with R⁷ and R⁸ substituents]

wherein $R^7$ and $R^8$ are independently H, Cl, F, methyl, halomethyl, methoxy, or halomethoxy.

3. A compound of claim 2 wherein $R^7$ and $R^8$ are independently F or Cl.

4. A compound of claim 3 wherein $R_7$ and $R^8$ are both F.

5. A compound of claim 3 wherein $R^7$ and $R^8$ are both Cl.

6. A compound of claim 3 wherein $R^7$ is F and $R^8$ is Cl.

7. A compound of claim 1 wherein $R^1$ is $CH_3$.

8. A compound of claim 1 wherein $R^2$ and $R^3$ are independently selected from H, halo, methyl, and methoxy.

9. A composition for controlling insects or mites which comprises a compound of claim 1 in combination with a phytologically-acceptable carrier.

10. A method of controlling insects or mites which comprises applying to a locus where control is desired an insect- or mite-inactivating amount of a compound of claim 1.

11. A method of controlling whitefly which comprises applying to a locus where control is desired a whitefly inactivating amount of a compound of claim 1.

12. A method of controlling mites which comprises applying to a locus where control is desired a mite-inactivating amount of a compound of claim 1.

13. A method of controlling aphids which comprises applying to a locus where control is desired an aphid inactivating amount of a compound of claim 1.

14. A method of protecting a plant from aphids, mites, or insects which comprises treating plant seed prior to planting it, treating soil where plant seed is to be planted, or treating soil at the roots of a plant after it is planted, with an effective amount of a compound of claim 1.

* * * * *

UNITED STATES PATENT AND TRADEMARK OFFICE
CERTIFICATE OF CORRECTION

PATENT NO. : 6,413,997 B1
DATED : July 2, 2002
INVENTOR(S) : Francis E. Tisdell, Peter L. Johnson, James T. Pechacek, Robert G. Suhr, Donald H. DeVries, Carl P. Denny and Mary L. Ash It is certified that error appears in the above-identified patent and that said Letters Patent is hereby corrected as shown below:

<u>Column 62,</u>
Line 26, should read -- ...alkyl, $(C_1-C_7)$ alkoxy, halo $(C_1-C_7)$ alkoxy, ... -- rather than "...alkyl, $(C_1-C_7)$ alkoxy, halo $(C_1-C_7)$ alkoxl, ..."
Line 32, should read -- ...from halo, $(C_1-C_{10})$ alkyl, branched $(C_3-C_6)$ alkyl, ... -- rather than "...from halo, $(C_1-C_{10})$ alkyl, branched $(C_{3-6})$ alkyl, ..."
Line 56, should read -- ...4. A compound of claim 3 where $R^7$ and $R^8$ are both F. -- rather than "...4. A compound of claim 3 where $R_7$ and $R^8$ are both F."

Signed and Sealed this

Nineteenth Day of November, 2002

*Attest:*

*Attesting Officer*

JAMES E. ROGAN
*Director of the United States Patent and Trademark Office*